(12) United States Patent
Peritt et al.

(10) Patent No.: US 11,904,081 B2
(45) Date of Patent: Feb. 20, 2024

(54) SYSTEMS AND METHODS FOR CLOSED LOOP, REAL-TIME MODIFICATIONS OF PATIENT CELLS

(71) Applicant: LUPAGEN, INC., Irving, TX (US)

(72) Inventors: David Peritt, Irving, TX (US);
Nripendra Das, Irving, TX (US)

(73) Assignee: Lupagen, Inc., Irving, TX (US)

( * ) Notice: Subject to any disclaimer, the term of this patent is extended or adjusted under 35 U.S.C. 154(b) by 771 days.

(21) Appl. No.: 17/054,734

(22) PCT Filed: May 13, 2019

(86) PCT No.: PCT/US2019/032022
§ 371 (c)(1),
(2) Date: Nov. 11, 2020

(87) PCT Pub. No.: WO2019/217964
PCT Pub. Date: Nov. 14, 2019

(65) Prior Publication Data
US 2021/0244871 A1    Aug. 12, 2021

Related U.S. Application Data

(60) Provisional application No. 62/670,528, filed on May 11, 2018, provisional application No. 62/670,516, filed on May 11, 2018.

(51) Int. Cl.
*A61M 1/34* (2006.01)
*A61M 1/36* (2006.01)

(52) U.S. Cl.
CPC ........ *A61M 1/3486* (2014.02); *A61M 1/3496* (2013.01); *A61M 1/3687* (2013.01); *A61M 1/3693* (2013.01); *A61M 1/3622* (2022.05); *A61M 2205/3306* (2013.01); *A61M 2205/3368* (2013.01)

(58) Field of Classification Search
CPC .............. A61M 1/3486; A61M 1/3496; A61M 1/3687; A61M 1/3693; A61M 1/3622; A61M 2205/3306; A61M 2205/3368; A61M 1/0281; A61M 2202/0411; A61M 2202/0439; A61P 35/00; C07K 14/7051; A61B 5/15003; A61B 5/150992; A61K 2039/5154
See application file for complete search history.

(56) References Cited

U.S. PATENT DOCUMENTS

| 6,773,669 | B1 | 8/2004 | Holaday et al. |
| 2004/0029240 | A1 | 2/2004 | Acker |
| 2005/0173315 | A1* | 8/2005 | Bosch ............... A61P 37/02 210/651 |
| 2011/0104128 | A1 | 5/2011 | Cooper et al. |
| 2016/0339165 | A1* | 11/2016 | Perritt ................ A61P 7/00 |
| 2017/0049951 | A1 | 2/2017 | Abedin et al. |
| 2020/0179582 | A1 | 6/2020 | McAfee et al. |
| 2020/0282116 | A1 | 9/2020 | Min et al. |

FOREIGN PATENT DOCUMENTS

| EP | 3034105 B1 | 8/2018 |
| EP | 3632484 A1 | 4/2020 |
| WO | 2010075061 A3 | 7/2010 |
| WO | 2019046766 A2 | 3/2019 |

* cited by examiner

Primary Examiner — Nelson B Moseley, II
(74) Attorney, Agent, or Firm — Rimon PC

(57) ABSTRACT

Provided herein are bedside systems and methods for performing customized cell-based therapies and treatments in a patient-connected, closed-loop continuous-flow manner, including cellular modifications and treatments, e.g., to produce chimeric antigen receptor-T (CAR-T) cells among other cellular modifications and treatments.

19 Claims, 3 Drawing Sheets

SYSTEMS AND METHODS FOR CLOSED LOOP, REAL-TIME MODIFICATIONS OF PATIENT CELLS

CROSS-REFERENCE TO RELATED APPLICATIONS

This application is a United States national stage entry of an International Application serial no. PCT/US2019/032022 filed May 13, 2019 which claims priority to U.S. provisional application Ser. No. 62/670,516 filed May 11, 2018, and U.S. provisional application Ser. No. 62/670,528 filed May 11, 2018. The contents of these applications are incorporated herein by reference in their entirety as if set forth verbatim.

BACKGROUND OF THE INVENTION

Blood cells are produced continuously over the life of an individual and derive from hematopoietic stem cells (HSC). HSCs are primarily found in the bone marrow and give rise to hematopoietic progenitor cells (HPC) and to blood cells of the various cell types (e.g., red blood cells (RBC) and leukocytes or white blood cells (WBC)).

Apheresis is a medical procedure in which the blood of an individual is passed through an apparatus, yielding a predominant constituent (e.g., nucleated blood cells or leukocytes), and returning the other constituents to the circulation. Historically, apheresis is in general a three-step process comprising: (1) withdrawing blood from the individual, (2) separating the blood components, and (3) returning one or more component(s) of the blood to the individual. Various types of apheresis procedures can be used depending on the component of blood that is being removed. For example, "plasmapheresis" generally refers to the separation and collection of blood plasma, "thrombocytapheresis" refers to the separation and collection of platelets, and "leukapheresis" usually refers to the separation and collection of leukocytes (WBC).

SUMMARY

Provided herein are bedside systems and methods for performing customized cell-based therapies and treatments in a patient-connected, closed-loop continuous-flow manner, including cellular modifications and treatments, e.g., to produce chimeric antigen receptor-T (CAR-T) cells among other cellular modifications and treatments. FIG. 1 is a block diagram illustrating an exemplary embodiment of a system described herein, by which blood is removed from a patient, processed, customized, and returned to the patient primarily in a closed-loop, continuous-flow manner at the patient's bedside. As shown, an arrangement of modules and units are used that are sequentially used for separation and collection of target cells from whole blood, employing for example, leukapheresis and/or other cell enrichment techniques, optionally including cell enrichment, purification and/or washing using an elutriation device, followed by one or more cell customization procedures, e.g., to generate patient-specific CAR-T cells, optionally followed by cell enrichment, purification, fractionation, and/or washing, after which the processed and modified fraction comprising CAR-T cells are returned to the patient by means of an outlet conduit.

Chimeric antigen receptors (CARs) represent modified T cell receptors, where the antigen binding domain is replaced with the antigen binding domain of an antibody that specifically binds a desired target antigen. T cells expressing such CARs are termed "CAR T cells" and provide a way to direct a cytotoxic T cell response to target cells expressing a selected target antigen, most often a tumor antigen or tumor-associated antigen. Engagement of the target antigen on the surface of a target cell by a CAR expressed on a CAR T cell promotes killing of the target cell.

Systems and methods as described herein permit the removal and customization or modification of target nucleated blood cells from a patient in real time, without the need for ex vivo expansion, incubation, and/or other manipulation of cells common, for example, in some gene or cell therapeutic approaches. In the systems and methods described herein, any necessary expansion, activation, and/or maturation of the customized or modified cells, e.g., patient-specific CAR-T cells, occur in the patient (in vivo). While some embodiments may permit testing or analysis of a sample of cells removed from the system, e.g., to evaluate efficiency of customization or other parameters, the systems described herein generally avoid operations or incubations performed outside the subject systems on cells to be re-administered to the patient.

According to frequently contemplated embodiments, a subject-connected, closed-loop system for the modification of a cell, system is provided comprising: a) an inlet conduit adapted for parenteral communication with the subject and adapted for receiving blood from the subject; b) a cell separation module in fluid communication with the inlet conduit, the cell separation module comprising a cell separator configured to produce a fraction enriched in a target nucleated blood cell type using the blood from the subject, and the cell separation module further comprising a first sampling unit for obtaining a sample of the fraction; c) a cell customization module in fluid communication with the cell separation module so as to receive the nucleated blood cell fraction enriched in the target cell type from the cell separation module, the cell customization module configured to present one or more modifying agents to the target nucleated blood cells, thereby generating modified cells, and the cell customization module further comprising a second sampling unit for obtaining a sample of the modified cells; d) a detector configured to conduct a detection operation and operably interfaced with the cell separation module, the cell customization module, operably interfaced between the cell separation module and the cell customization module, and/or operably interfaced between the cell customization module or the cell separation module and the subject; e) an outlet conduit adapted for parenteral communication with the subject and for conducting modified target cells parenterally to the subject; and f) a processor configured to control an operation of the inlet conduit, the cell separation module, the cell customization module, the detector, or the outlet conduit of the system; wherein the inlet conduit, the cell separation module, the cell customization module, the detector, and the outlet conduit of the system are connected in a fluid-sealed closed-loop adapted for parenteral connection with a patient at both ends of the fluid sealed closed-loop, and the system is configured to permit cell separation, delivery of a modifying agent to the target nucleated blood cell type and delivery of the modified cells to the subject in real time within the fluid sealed closed-loop. Such contemplated systems are generally bedside systems fully integrated in a single housing or instrument.

Accordingly, subject-connected, closed-loop systems for the modification of a cell are provided herein, such systems comprising:
  a) an inlet conduit for receiving blood from a subject;
  b) a cell separation module coupled to the inlet conduit, the cell separation module comprising a cell separator configured to produce a fraction enriched in target nucleated blood cells;
  c) a cell customization module, coupled to the cell separation module so as to receive the nucleated blood cell fraction enriched in the target cell type, the cell customization module configured to deliver one or more modifying agents to the target nucleated blood cells, thereby generating modified cells;
  d) at least one detector module interfaced with one or more modules of the system;
  e) an outlet conduit for conducting modified target cells back to the subject; and
  f) a processor configured to control the operation of the system;
the system configured to permit cell separation, delivery of a modifying agent to a target cell type and return of modified target cells to the subject in real time in a closed loop.

Also, subject-connected, closed-loop systems for generating chimeric antigen receptor (CAR) T cells are provided herein, comprising:
  a) an inlet conduit for receiving blood from a subject;
  b) a cell separation module coupled to the inlet conduit, the cell separation module comprising a cell separator configured to produce a fraction enriched in target nucleated blood cells;
  c) a cell customization module, coupled to the cell separation module so as to receive the nucleated blood cell fraction enriched in the target cell type, the cell customization module configured to deliver one or more nucleic acids encoding a CAR to the target nucleated blood cells, thereby generating CAR T cells;
  d) at least one detector module interfaced with one or more modules of the system;
  e) an outlet conduit for conducting modified target cells back to the subject; and
  f) a processor configured to control the operation of the system;
the system configured to permit cell separation, delivery of a nucleic acid encoding a CAR to a target cell type to generate CAR T cells, and return of CAR T cells to the subject in real time in a closed loop.

In certain embodiments of these aspects and all such aspects described herein, the at least one detector module detects modified cells and sends a signal when a threshold level of modified cells is reached.

In certain embodiments of these aspects and all such aspects described herein, the cell customization module comprises an electroporation chamber, connected to a power source effective to electroporate the nucleic acid into a target nucleated blood cell.

In certain embodiments of these aspects and all such aspects described herein, the cell customization module interfaces with a detector module.

In certain embodiments of these aspects and all such aspects described herein, the cell customization module comprises an inlet for introducing a nucleic acid preparation to a suspension of washed cells, or a chamber comprising a nucleic acid preparation encoding a CAR into which a washed cell suspension is introduced, the nucleic acid preparation comprising a lipid transfection reagent.

In certain embodiments of these aspects and all such aspects described herein, the cell customization module interfaces with a detector module.

In certain embodiments of these aspects and all such aspects described herein, the cell customization module comprises:
  a temperature controlled holding unit capable of reaching and maintaining temperatures between 0° C. and 37° C., inclusive;
  a cell washing unit comprising a chamber that mixes target nucleated blood cells with at least one wash solution that dilutes or removes a plasma component from the target nucleated blood cells and places washed cells into suspension prior to their modification;
  buffer exchange;
  cell washing post electroporation;
  cell purification, e.g., by buoyant beads using the elutriator;
  an inlet for introducing a nucleic acid preparation to the suspension of washed cells, or a chamber comprising a nucleic acid preparation into which a washed cell suspension is introduced; and
  an electroporation chamber, connected to a power source effective to electroporate the nucleic acid into a target nucleated blood cell.

In certain embodiments, the cell customization module comprises: a temperature control unit capable of reaching and maintaining temperatures within the unit of between 0° C. and 37° C., inclusive; a cell washing unit comprising a chamber that mixes target nucleated blood cells with at least one wash solution that dilutes or removes a plasma component from the target nucleated blood cells and places washed cells into suspension prior to their modification; an inlet for introducing a nucleic acid preparation to the suspension of washed cells, or a chamber comprising a nucleic acid preparation into which a washed cell suspension is introduced; and an electroporation chamber, connected to a power source effective to electroporate the nucleic acid into a target nucleated blood cell, wherein temperature control unit, the cell washing unit, and the electroporation chamber are positioned in the temperature control unit.

In certain embodiments of these aspects and all such aspects described herein, the cell customization module comprises: a temperature control unit capable of reaching and maintaining temperatures between 4° C. and 37° C., inclusive; a cell-washing unit comprising a chamber that mixes target nucleated blood cells with at least one wash solution that dilutes or removes a plasma component from the target nucleated blood cells and places washed cells into suspension prior to their modification; and an inlet for introducing a nucleic acid preparation to the suspension of washed cells, or a chamber comprising a nucleic acid preparation into which a washed cell suspension is introduced, the nucleic acid preparation comprising a lipid transfection reagent.

In certain embodiments of these aspects and all such aspects described herein, the cell customization module comprises:
  a chamber in fluid communication with and configured to receive a suspension of enriched target nucleated blood cells from the cell separation module, the chamber comprising an inlet for the introduction of a modifying agent or comprising a preparation of modifying agent, and a plurality of microfluidic channels that narrow over their length to at least 20-99% of the diameter of the enriched target nucleated blood cells; and a source of pressure sufficient to force suspended cells through the plurality of microfluidic channels in the presence of the modifying agent.

In certain embodiments of these aspects and all such aspects described herein, the cell customization module interfaces with a detector module.

In certain embodiments of these aspects and all such aspects described herein, the cell customization module comprises:
- a temperature control unit capable of reaching and maintaining temperatures between 4° C. and 37° C., inclusive;
- a cell-washing unit comprising a chamber that mixes target nucleated blood cells with at least one wash solution that dilutes or removes a plasma component from the target nucleated blood cells and places washed cells into suspension prior to their modification; and
- an inlet for introducing one or more modifying agents to the suspension of washed cells, or a chamber comprising one or more modifying agents into which a washed cell suspension is introduced, thereby allowing contacting of the washed cells with the one or more modifying agents.

In certain embodiments of these aspects and all such aspects described herein, the cell customization module comprises:
- a temperature control unit capable of reaching and maintaining temperatures between 4° C. and 37° C., inclusive;
- a cell-washing unit comprising a chamber that mixes target nucleated blood cells with at least one wash solution that dilutes or removes a plasma component from the target nucleated blood cells and places washed cells into suspension prior to their modification; and
- an inlet for introducing one or more modifying agents in a membrane disruptive delivery solution to the suspension of washed cells, or a chamber comprising one or more modifying agents in a membrane disruptive delivery solution into which a washed cell suspension is introduced thereby allowing contacting of the washed cells with the one or more modifying agents in the membrane disruptive solution.

Often, cell washing units of the presently contemplated embodiments provide buffer exchange, concentration of cells, cell washing, cleaning of nucleated cells from, e.g., platelets, PMNs, junk, dead cells, etc., and readying of the cells for electroporation and/or washes customized cells in buffer such as saline for return into human blood.

According to often included embodiments, a detector/detector module of the system is interfaced with the cell customization module and configured to detect and count modified cells and send a signal to the processor when a threshold level of the modified cells is present.

In certain embodiments of these aspects and all such aspects described herein, the system further comprises a sampling module configured to receive an aliquot of cell suspension from the cell customization module.

In certain embodiments of these aspects and all such aspects described herein, the sampling module interfaces with a detector/detector module.

In certain embodiments of these aspects and all such aspects described herein, the detector module detects when the aliquot of cell suspension comprises a predetermined threshold of modified (e.g., CAR T) cells.

In certain embodiments of these aspects and all such aspects described herein, the cell customization module does not release the modified (e.g., CAR T) cells to the outlet conduit until the predetermined threshold is reached in the sampling module.

In certain embodiments of these aspects and all such aspects described herein, the cell customization module is configured to allow for batch-flow operation.

In certain embodiments of these aspects and all such aspects described herein, the cell separation module comprises a leukapheresis unit that separates nucleated blood cells from a nuclear red blood cells.

In certain embodiments of these aspects and all such aspects described herein, the cell separation module further comprises an enrichment unit for further selecting a subset of target nucleated blood cells to enter the cell customization module.

In certain embodiments of these aspects and all such aspects described herein, the enrichment unit comprises a reagent that specifically binds a cell-surface determinant on nucleated blood cells other than the subset of target nucleated blood cells, thereby selectively enriching for the subset of target nucleated blood cells.

In certain embodiments of these aspects and all such aspects described herein, the reagent that specifically binds the cell surface determinant on nucleated blood cells other than the subset of target nucleated blood cells is attached to a solid support or magnetic beads.

In certain embodiments of these aspects and all such aspects described herein, the enrichment unit comprises a reagent that specifically binds a cell-surface determinant present on the subset of target nucleated blood cells, thereby selectively enriching for the subset of target nucleated blood cells.

In certain embodiments of these aspects and all such aspects described herein, the reagent that specifically binds the cell surface determinant present on the subset of target nucleated blood cells is attached to a solid support or magnetic beads.

In certain embodiments of these aspects and all such aspects described herein, the enrichment unit selects the subset of target nucleated blood cells using one or more parameters selected from cell size, cell shape, cell granularity, cell buoyancy, cell acoustics, and cell density.

In certain embodiments of these aspects and all such aspects described herein, the system further comprises a purification module for selecting the modified (e.g., CAR T) cells.

In certain embodiments of these aspects and all such aspects described herein, the purification module comprises a washing unit.

In certain embodiments of these aspects and all such aspects described herein, the purification module interfaces with a detector/detector module.

In certain embodiments of these aspects and all such aspects described herein, the purification module comprises a reagent that specifically binds a cell-surface determinant on cells other than the modified (e.g., CAR T) cells, thereby selectively enriching for the modified cells.

In certain embodiments of these aspects and all such aspects described herein, the reagent that specifically binds the cell surface determinant on cells other than the modified cells is attached to a solid support or magnetic beads.

In certain embodiments of these aspects and all such aspects described herein, the purification module comprises a reagent that specifically binds a cell-surface determinant present on the modified CAR T cells, thereby selectively enriching for the modified cells.

In certain embodiments of these aspects and all such aspects described herein, the reagent that specifically binds the cell surface determinant present on the modified (e.g., CAR T) cells is attached to a solid support or magnetic beads.

In certain embodiments of these aspects and all such aspects described herein, the purification module selects the modified (e.g., CAR T) cells using one or more parameters selected from cell size, cell shape, cell granularity, cell buoyancy, cell acoustics, and cell density.

In certain embodiments of these aspects and all such aspects described herein, the modifying agent is selected from a small molecule agent, a biologic agent, a protein or peptide therapeutic, and a nucleic acid therapeutic.

In certain embodiments of these aspects and all such aspects described herein, the cell customization module comprises an inlet for introduction of a preparation comprising the cell-surface determinant or a mimic thereof to competitively elute cells bound to the solid support after delivery of the modifying agent or nucleic acid to enriched target cells.

In certain embodiments of these aspects and all such aspects described herein, the detector comprises two or more detectors. Often the detector/detector module comprises an optical detector. In some embodiments of these aspects and all such aspects described herein, the detector module comprises a fluorescence or acoustical detector. Often, the detector comprises two or more detectors selected from the group consisting of an optical detector, a fluorescence detector, and an acoustical detector.

In certain embodiments of these aspects and all such aspects described herein, the cell customization module comprises a conduit that permits a first batch of target cells treated with a modifying agent to pass into a temperature-controlled holding unit while a second batch is treated with modifying agent.

In certain embodiments of these aspects and all such aspects described herein, the holding unit interfaces with the detector module.

In certain embodiments of these aspects and all such aspects described herein, the detector module detects the number of cells in the holding unit or expression of a marker of target cell modification by cells in the holding unit or both.

In certain embodiments of these aspects and all such aspects described herein, a signal from the detector module initiates transfer of modified (e.g., CAR T) cells from the cell customization module to the subject through the outlet conduit.

In certain embodiments of these aspects and all such aspects described herein, one or both of the cell-separation and cell customization modules comprises a single-use cassette or system kit.

In certain embodiments of these aspects and all such aspects described herein, the modifying agent comprises a nucleic acid.

In certain embodiments of these aspects and all such aspects described herein, the nucleic acid encodes a therapeutic polypeptide.

In certain embodiments of these aspects and all such aspects described herein, the nucleic acid encodes a chimeric T cell receptor.

In certain embodiments of these aspects and all such aspects described herein, the target nucleated blood cell comprises a lymphoid cell or a myeloid cell.

In certain embodiments of these aspects and all such aspects described herein, the lymphoid cell is selected from a T cell, a B cell, and an NK cell.

In certain embodiments of these aspects and all such aspects described herein, the cell separation module enriches for CD34+ stem cells. In such examples, CD34+ stem cells are edited to impart one or more traits or to correct genetic defects such as beta thalassemia, sickle cell, HIV CCR5 knockouts, among others.

In certain embodiments of these aspects and all such aspects described herein, the modification comprises a SLIPSTREAM™ process of producing a deep-primed T Cell.

In certain embodiments of these aspects and all such aspects described herein, the myeloid cell is selected from a monocyte, a macrophage, a neutrophil, a basophil, an eosinophil, a dendritic cell and a megakaryocyte. In such examples, macrophages and/or dendritic cells are adapted for vaccination for infectious disease or cancer.

According to frequently included embodiments, a bedside system adapted for treatment of a disease or condition involving blood cells, needing immunomodulation, and/or having systemic involvement is provided. In often in included embodiments, the disease or condition comprises cancer, sickle cell anemia, hemophilia and/or beta-thalassemia.

Also provided herein, in certain aspects, are methods of generating CAR T cells from a target nucleated blood cell, the method comprising connecting the circulation of a subject in need of such CAR T cells to any of the systems described herein via the inlet and outlet conduits.

In certain contemplated embodiments, the one or more modifying agents contemplated for use in the systems contemplated herein comprise a nucleic acid encoding a Clustered Regularly Interspaced Short Palindromic Repeats (CRISPR) enzyme comprising one or more nuclear localization sequences.

Often according to presently contemplated embodiments, the processor module of the system is placed in operable connection with: the detector to control and/or monitor the status, operation and/or function of one or more detector; the cell separation module to control and/or monitor the status, operation and/or function of cell separation, cell washing, and/or cell enrichment; the cell washing unit or a conduit or flow path within the system to control and/or monitor the status, operation and/or function of cell washing, and/or cell/fluid flow rate or direction; and/or the cell customization module to control and/or monitor the status, operation and/or function of purification, drug/genetic material administration, electroporation, microfluidic transfection, lipofection, cell washing, and/or incubation. In often contemplated embodiments, the system is remotely controlled and/or monitored.

Often according to presently contemplated embodiments, a method of introducing a modification to a target nucleated blood cell is provided, the method comprising: parenterally (i.e., intravenously) connecting a subject in need of such modification to the subject-connected, closed-loop system via the inlet and outlet conduits; permitting the blood of the subject to flow into the cell separation module and producing a fraction enriched in a target nucleated blood cell type; permitting a blood cell fraction enriched in the target cell type to flow from the cell separation module to the cell customization module and contacting the blood cell fraction enriched in the target cell type with one or more modifying agents, thereby generating modified cells; and permitting the modified cells to parenterally flow to the subject via the outlet conduit.

Often, an aliquot of the fraction enriched in the target nucleated blood cell type is obtained and evaluated prior to permitting the fraction or a part thereof to flow to the cell customization module. Also often, an aliquot of the modified cells is obtained and evaluated prior to permitting the modified cells to flow to the outlet port.

According to frequently contemplated embodiments, a step of operably connecting a single use cassette or system kit adapted to introduce the modification to the target nucleated blood cell with the system is provided. Often, an operation of the system or a module thereof is controlled or monitored using a processor module. Also often, the processor is remotely controlled or monitored.

According to frequently contemplated embodiments, a subject-connected, closed-loop system for the modification of a cell is provided, wherein the cell customization module is configured to deliver one or more nucleic acids encoding a chimeric antigen receptor (CAR) to the target nucleated blood cells, thereby generating CAR T cells; and wherein the system is further configured to permit cell separation, delivery of a nucleic acid encoding a CAR to a target cell type to generate CAR T cells, and return of CAR T cells to the subject in real time in a closed loop. Often, the detector detects when the aliquot comprises a predetermined threshold of modified CAR T cells. In frequent embodiments, the cell customization module is configured to store and not release the modified CAR T cells to the outlet conduit until the predetermined threshold is reached in the sampling module. Also often, the system further comprises a cell purification module for selecting the modified CAR T cells.

In certain other frequent embodiments, a method of generating CAR T cells from a target nucleated blood cell is provided, the method comprising: parenterally (e.g., intravenously) connecting a subject in need of such CAR T cells to the subject-connected, closed-loop system via the inlet and outlet conduits; permitting the blood of the subject to flow into the cell separation module and producing a fraction enriched in a target nucleated blood cell type; permitting a blood cell fraction enriched in the target cell type to flow from the cell separation module to the cell customization module and contacting the blood cell fraction enriched in the target cell type with one or more modifying agents, thereby generating CAR T cells; and permitting the CAR T cells to parenterally flow to the subject via the outlet conduit.

In some embodiments of these aspects and all such aspects described herein, the modification comprises introduction of a nucleic acid or polypeptide to a target nucleated blood cell.

In some embodiments of these aspects and all such aspects described herein, the target nucleated blood cell is selected from the group consisting of B cells, T cells, activated or regulatory T cells, dendritic cells, plasmacytoid dendritic cells, natural killer cells, macrophages, monocytes, and plasma cells.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, "chimeric antigen receptor T cells" or "CAR T cells" refer to a T cell or population thereof, which has been modified through molecular biological methods to express a chimeric antigen receptor (CAR) on the T cell surface. The CAR is a polypeptide having a pre-defined binding specificity to a desired target expressed operably connected to (e.g., as a fusion, separate chains linked by one or more disulfide bonds, etc.) the intracellular part of a T-cell activation domain. By bypassing MHC class I and class II restriction, CAR engineered T cells of both CD8+ and CD4+ subsets can be recruited for redirected target cell recognition. The most common CARs are fusions of immuoglobulin binding functionality (e.g., as a single-chain variable fragment (scFv) derived from a monoclonal antibody) to CD3-zeta (CD3.zeta.) transmembrane and endodomain. Such molecules result in the transmission of a zeta signal in response to recognition by the immuoglobulin binding functionality of its target. There are, however, many alternatives. By way of example, an antigen recognition domain from native T-cell receptor (TCR) alpha and beta single chains can also be used as the binding functionality. Alternatively, receptor ectodomains (e.g., CD4 ectodomain) or cytokines (which leads to recognition of cells bearing the cognate cytokine receptor) can be employed. All that is required of the binding functionality is that it binds a given target with high affinity in a specific manner.

As used herein, "closed-loop" refers to a system wherein at least a sub-population of cells is kept in a system that is a continuous flow-through, such that the cells are derived from the patient and can be modified and returned to the patient without being moved off-line.

As used herein, "continuous flow" refers to the flow of blood from a patient to the modular bedside system and back to the patient in which non-target cells generally return to the patient whereas target cells can be customized by a customization module in the device and then returned to the patient; all in a closed-loop, patient-connected manner and in real-time. The term "continuous flow" does not exclude operations within a closed-loop system that occur while a cell population or sub-population is shunted or deposited for some period of time, into a holding, sampling or incubating chamber or receptacle within the system.

"Discontinuous" refers to not being part of a closed-loop.

"Patient-connected" or "bedside" refers to when the system is connected to the patient. Preferably, the patient can be connected to the system for the entire period of blood cell separation, enrichment, customization, and purification. The blood flows from the patient to the system and back to the patient in which non-target cells generally return to the patient, whereas target cells are customized and then returned to the patient.

As used herein, the term "consisting essentially of" refers to those elements for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, "treatment" means any way the symptoms of a condition, disorder or disease are ameliorated or otherwise beneficially altered.

As used herein, "subject" often refers to an animal, including, but not limited to, a primate (e.g., human). The terms "subject" and "patient" are used interchangeably herein.

As used herein, the terms "detect," "detecting," or "detection" may describe either the general act of discovering or discerning or the specific observation of a molecule, cell or composition, whether directly or indirectly labeled with a detectable label.

All patents, patent applications, and publications mentioned herein, both supra and infra, are hereby incorporated by reference in their entireties.

DETAILED DESCRIPTION

The systems, devices, and methods described herein allow for customizing and modifying cells, including specific sub-populations of cells, and provide means of performing cell-based therapies and treatments in a patient-connected manner that can done at the patient's bedside and can use continuous-flow technology. More specifically, systems, devices, and methods are provided herein that allow for the concurrent collection and enrichment of specific target cells from a subject's peripheral blood that are modified or treated within one or more modules of the system and returned to the subject, concurrently with or after the remaining blood components are returned to the subject. The various embodiments of the systems and methods described herein allow for efficient, patient-specific customization of target cell populations via, for example, nucleic acid and protein-based modifications and therapies involving electroporation, lipofection and/or transfection, as well as through the addition of small molecule drugs, biologics, and other methods of cell activation/suppression. These systems and methods significantly reduce operating costs and improve efficiency, as well as improve patient safety and reduce risks of contamination and damage or loss to patient samples.

The systems, devices, and methods described herein allow for, e.g., preparing customized CAR-T cells for use in therapies and treatments in a patient-connected manner that can done at the patient's bedside using continuous-flow technology. More specifically, systems, devices, and methods are provided herein that allow for the concurrent collection and enrichment of specific target cells, such as lymphocytes, from a subject's peripheral blood that are modified or treated to become CAR-T cells and returned to the subject, concurrently with or after the remaining blood components are returned to the subject. These systems and methods significantly reduce operating costs and improve efficiency of CAR-T based therapies and treatments, as well as improve patient safety and reduce risks of contamination and damage or loss to patient samples.

Figure 1:
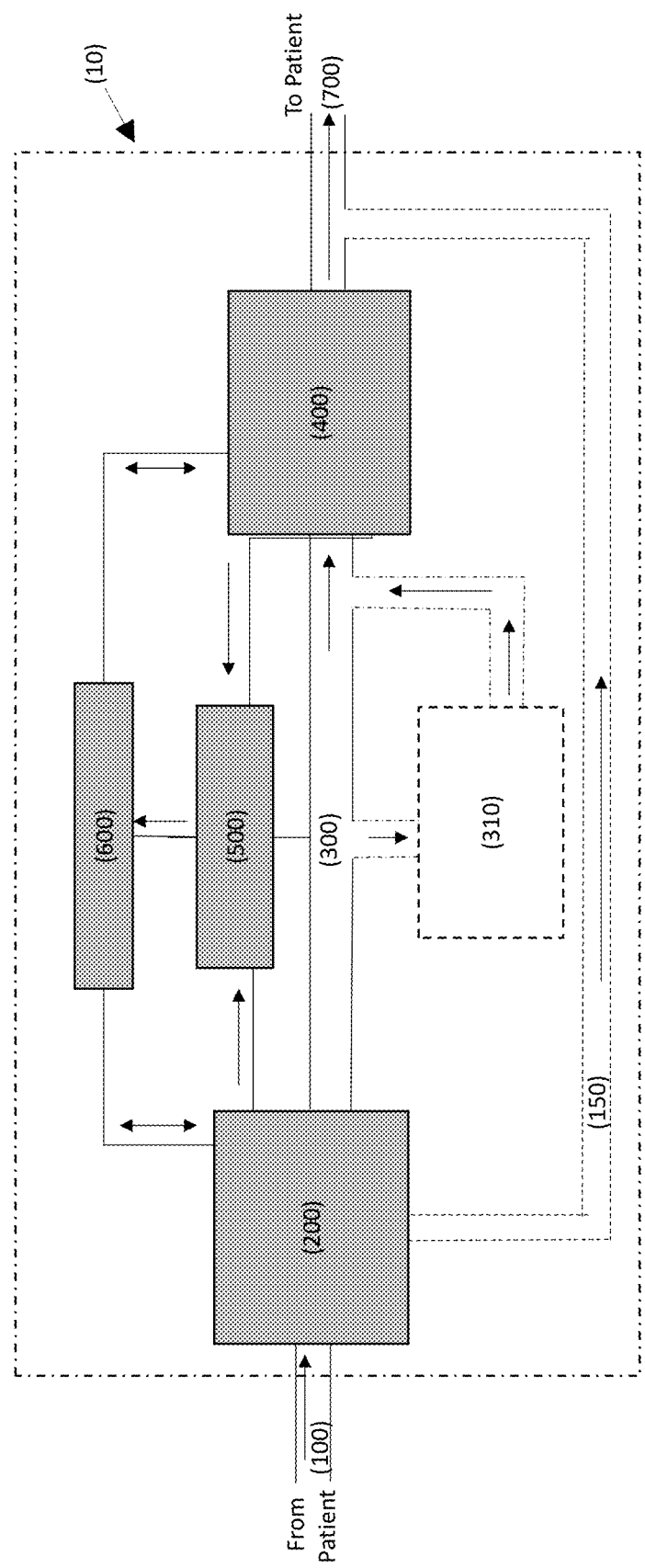
FIG. 1 depicts a schematic of an exemplary embodiment of a system for cell customization and modification described herein.

In one aspect, as depicted in FIG. 1, a system as described herein includes an inlet conduit (100) to receive blood from a subject or patient, connected to a cell separation module (200) that separates or enriches nucleated blood cells from whole blood and, optionally washes them or exchanges their medium for one better-suited for cell modification. The cell separation module (200) is connected via conduit or tubing (300) to a cell customization module (400), within which cells are customized by the introduction of one or more customization or modifying agents, as described herein. Customized cells flow or are pumped from cell customization module (400) back to the patient via outlet conduit or tubing (700). The cell separation module (200) is also connected to conduit or tubing (150), within which plasma, non-nucleated cells or other non-target cells, are returned to the subject through a conduit or tubing (700). The outlet conduit or tubing (700) can include a valve or port that permits flow-through of a blood fraction comprising that blood portion or portions that are not transmitted to the cell customization module, e.g., plasma, non-nucleated cells or other non-target cells, back to the patient or subject, while the customized cells are reintroduced to the patient or subject separately after the customization steps are completed. A system as described herein also includes at least one detector (500) that interfaces with one or more of the cell separation module (200), cell customization module (400), or a component thereof as described herein. A detector can detect, via an appropriate sensor, for example, the number of cells or some property of the cells or medium indicative of, for example, cell status, cell viability, cell modification or customization, etc., as discussed further herein below. In certain embodiments, there are a plurality of detectors (500) or sensors that detect various properties, at various points within the system to provide information to a processor (600) that controls the system and its various modules. The processor (600) is connected to each of the cell separation module (200), the cell customization module (400), and to the various components of these, as well as any pump(s), valves, or other components requiring control within the system.

FIG. 1 depicts the flow of blood from the patient via conduit (100) to the cell separation module (200) in a presently contemplated system (10). This cell separation module (200), depicted in FIG. 2, includes or connects with a cell washing unit (210), an enrichment unit (1100) and a sampling unit (450A). After passing through the cell separation module, nucleated cells are separated from non-nucleated cells and plasma. Non-nucleated cells and plasma leave the cell separation module via conduit (150). Nucleated cells then leave the cell separator module (200) via conduit (300), which may be operably connected with one or more detector (500). Nucleated target cells may then be washed before they leave the cell separation module or washed in cell washing unit (310), which unit can interface with processor module (600) and one or more detector (500), and to the cell customization module (400). The cell customization module depicted in greater detail in FIG. 3, includes or connects to a drug/genetic material administration port (405), a cell washing unit (410), a holding incubating unit (440), a sampling unit (450 B), and a cell purification unit (460). After the customized composition passes through the cell customization module, it returns to the patient via conduit (700), often combined with the non-nucleated cells and plasma previously separated from the patient blood.

Figure 2:
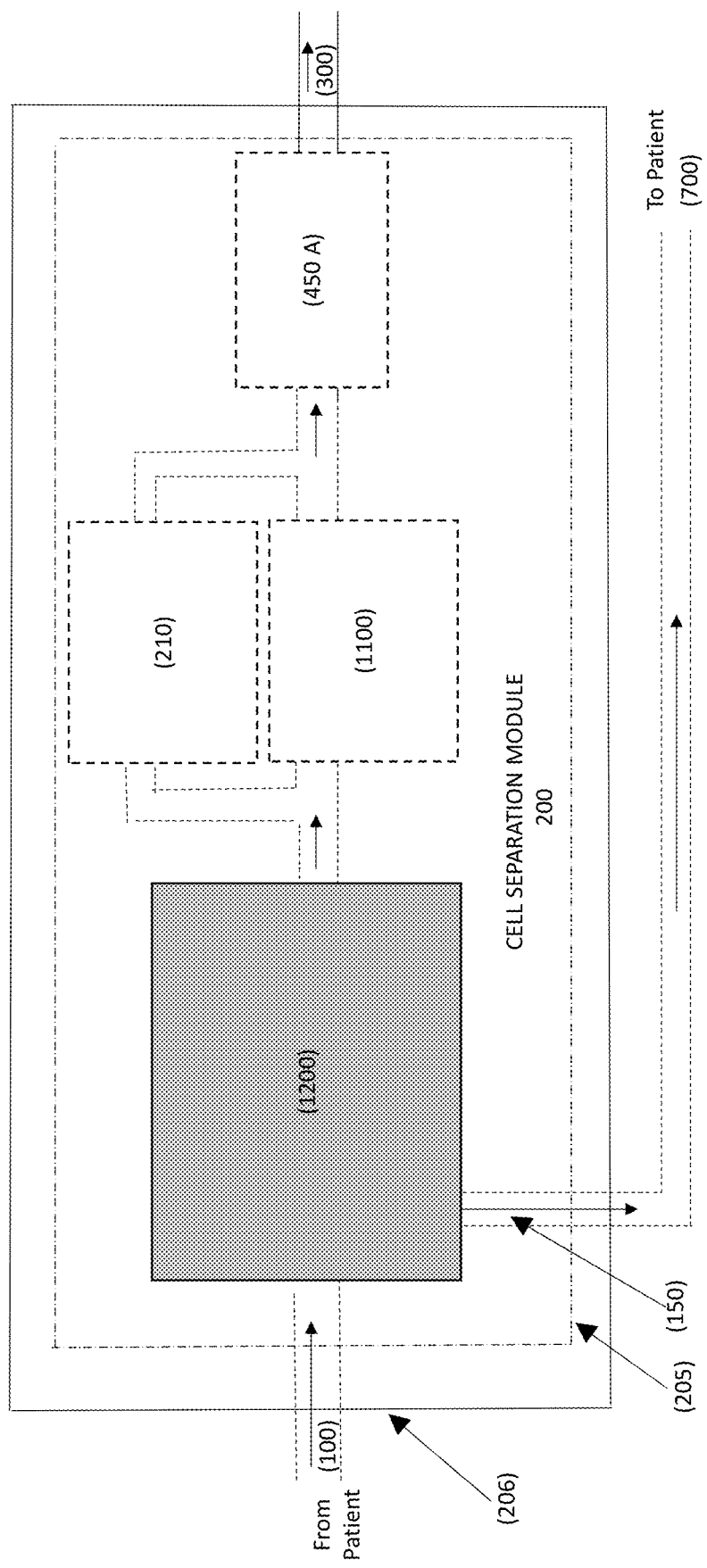
FIG. 2 provides a schematic illustrating various embodiments of a cell separation module (200) as described herein. The cell separation module includes a cell separator (1200) (e.g., apheresis device) that is connected directly to the subject via the inlet conduit (100) and conduit or tubing (150) for plasma, non-nucleated cells or other non-target cells, that are transported back to the subject via conduit (700). As described in further detail below, the cell separation module (200) shown in FIG. 2 illustrates the optional inclusion of an enrichment unit (1100), an/or a cell washing unit (210), an/or sampling unit (450A) in the cell separation module. The washing unit can be also used for buffer exchange which may be important for further unit operations such as electroporation both prior to the unit operation and prior to return to the patient.

FIG. 2 depicts a cell separation module (200), which may be optionally temperature controlled within housing/region (205). The temperature ranges contemplated within temperature-controlled region (205) are described herein. Optional housing (206) may enclose one or more devices, components, or units of the cell separation module (200). Housing (206) and temperature-controlled regions, while separately depicted may be the same regions. As noted above, blood from the patient flows in via conduit (100) to the cell separator (1200). After passing through the cell separator (1200), nucleated cells are separated from non-nucleated cells and plasma. Non-nucleated cells and plasma leave the cell separator (1200) via conduit (150). Nucleated cells pass through to a cell washing unit (210) and/or enrichment unit (1100). The cell washing unit (210) and enrichment unit (1100) may be connected such that cells flow in fluid composition to/from the enrichment unit (110) to/from the cell washing unit (210) in one or more cycles. This fluid composition may be sampled in sampling unit (450A) prior to the nucleated cells exiting via conduit (300). While the sampling unit (450A) is depicted after the cell washing unit (210) and enrichment unit (1100), the sampling port for the sampling unit (450A) may be positioned at or between one or more of these units. Often, sampling the fluid composition provides the indication about whether further washing or enrichment is needed or desired.

Figure 3:
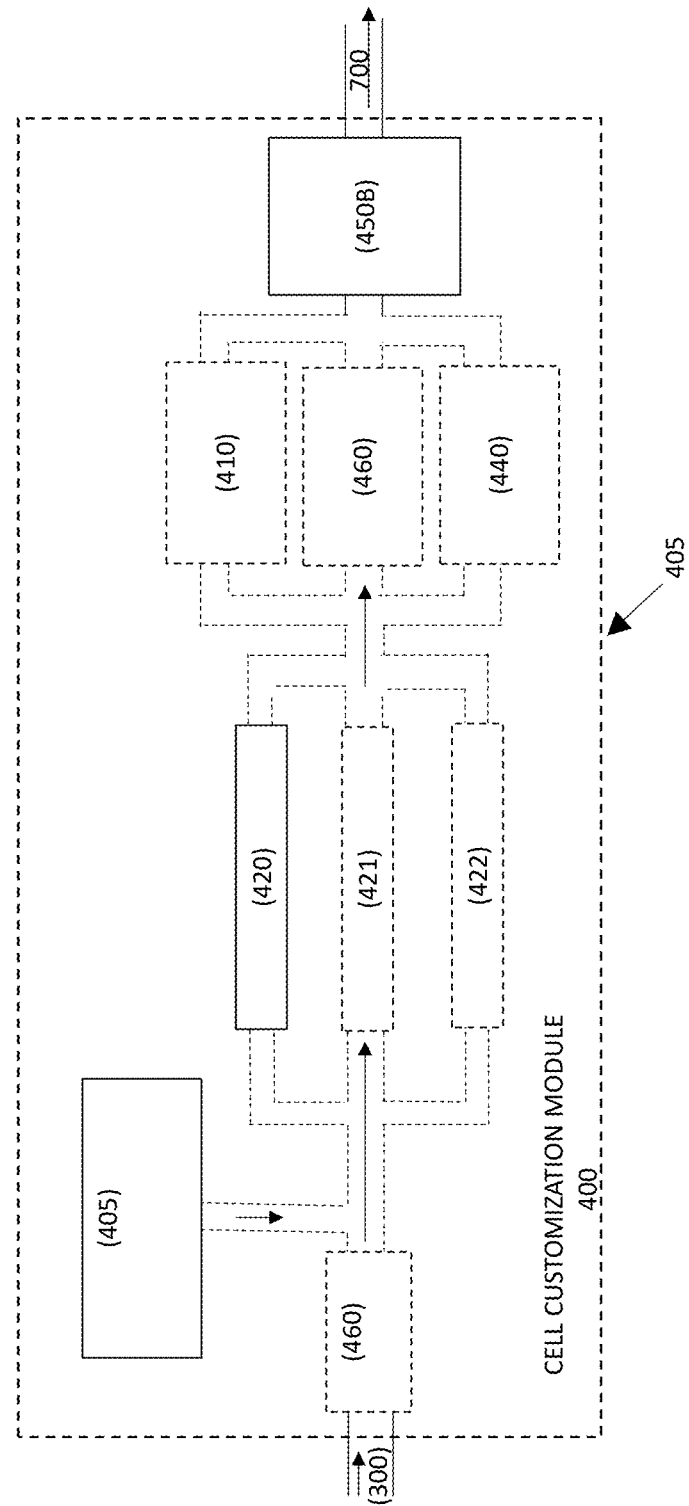
FIG. 3 provides a schematic illustrating various embodiments of a cell customization module as described herein. As described in further detail below, the cell customization module shown in FIG. 3 illustrates the optional inclusion of a cell purification module (460) within a cell customization module (400), drug or genetic material administration port (405), and alternative modules for cell customization processes including an electroporation module (420), a microfluidic module (421), a lipofection module (422) or other module (not shown) that permits the introduction of a cell customization agent to a cell. The purification module (460) may occur prior to or after the cell modification step. Optional sampling unit (450B), holding, incubation or collection unit (440) and purification modules (460) are included after the cell customization and prior to returning to patient via tubing (700).

FIG. 3 depicts a cell customization module (400), which may be optionally temperature controlled within optional housing/region (405). The temperature ranges contemplated within temperature-controlled housing/region (405) are described herein. Optional housing/region (405) may enclose one or more devices, components, modules or units of the cell customization module (400). As noted above, nucleated cells flow in via conduit (300) to the purification module (460). A drug/genetic material administration port (405) is provided for the introduction/contact of drug/genetic material to the nucleated cells if such material is not already included in the system (10) by virtue of a connected cassette/kit. This drug/genetic material administration port (405) may be provided in a different location or manner, depending on the specific electroporation (420), microfluidic (421), or lipofection (422) module that is utilized and the specific customization being performed. Nucleated cells then enter the electroporation (420), microfluidic (421), and/or lipofection (422) module. While all three modules are depicted within a single housing (405) and contemplated herein for use on a single of the presently described systems (10), often the system included one or more of these modules. For example, presently contemplated cell customization modules (400) and systems (10) may include one or more of an electroporation module (420), a microfluid module (421), and a lipofection module (422), each having the aspects and functions described herein. In certain embodiments, two or more of the same electroporation module (420), microfluid module (421), and/or lipofection module (422) are included in a single cell customization module (400) and system (10). In certain embodiments the fluidics of the cell customization module (400) permits flow of cells from one of an electroporation module (420), a microfluid module (421), and/or a lipofection module (422) to another of an electroporation module (420), a microfluid module (421), and/or a lipofection module (422) in a single system (10) before presenting the customized cells to the patent/subject via conduit (700). After the electroporation module (420), a microfluid module (421), and/or a lipofection module (422), cells pass into the cell washing unit (410), purification module (460) and/or holding/incubation unit (440). The cell washing unit (410), purification module (460) and holding/incubation unit (440) may be connected such that cells flow to/from each unit/module in one or more cycles. Samples of the cells may be obtained in sampling unit (450B) prior to exiting via conduit (700). While the sampling unit (450B) is depicted after the cell washing unit (410), purification module (460) and holding/incubation unit (440), the sampling port for the sampling unit (450B) may be positioned at or between one or more of these units/modules. While the purification module (460) is pictured twice in the Figure, it may be two separate purification modules but is usually is often a single purification module (460) and the multiple depictions are provided for simplicity of illustration relative to the direction of cell flow. Often, sampling of the cells provides an indication about whether further washing, purification and/or further incubation is needed desired. In certain embodiments, cells may be passed back to the electroporation module (420), a microfluid module (421), and/or a lipofection module (422) after passing through one or more of the cell washing unit (410), purification module (460) and holding/incubation unit (440) and before exiting in conduit (700).

The entire system (10) depicted in FIGS. 1-3, and described herein, is included within a single housing (e.g., line related to indicator 10) according to embodiments contemplated herein. This system is, in use, connected with a subject or patient in a closed-loop continuous-flow manner, from the patient to the inlet conduit (100) and through the system then to the output conduit (700) into the patent. In related embodiments, the entire system depicted in FIGS. 1-3, and described herein, is included within a single integrated mobile patient bed-side instrument according to embodiments contemplated herein. And, similarly, this system is, in use, connected with a subject or patient in a closed-loop continuous-flow manner, from the patient to the inlet conduit (100) and through the system then to the output conduit (700) into the patent.

In some embodiments, the system can execute a program of cell separation, optional cell washing, cell customization and optional purification and/or analysis before returning customized cells to the patient in an automated manner with no or minimal operator input once the program is initiated. In some embodiments, the system also comprises a pump/valve deck. While other pumps can be used, a peristaltic pump provides fluid transfer without undue shear forces introduced by some pumping mechanisms, and is well suited for the transport of cells in and through the systems described herein. Other reagents can be transferred into and out of the various chambers, units and modules via peristaltic pump or via a mechanical pump, e.g., with an impeller. In some embodiments, the cell separation module (200) interfaces with one or more detector modules, as described herein.

In various embodiments, the systems described herein permit the removal of nucleated blood cells from a patient or subject, customization or modification of at least a subset of those cells, and return of such cells to the patient in a closed loop format. As discussed above, this approach has benefits in terms of cost and reduced risk of contamination or supply chain issues, among others. An additional benefit for such embodiments is that the procedure obviates the need to expand cells ex vivo—the cells are treated, optionally incubated within the system for some period of time, then reintroduced to the patient via the outlet conduit. It is specifically contemplated that, in some embodiments, the patient is temporarily disconnected from the system for a period of time, while cells are processed in the system, but that cells remain within the system throughout the procedure. In other embodiments, a discontinuous system is contemplated, such that cells can be treated, e.g., to customize them, within the bedside system, but then all or a portion of the treated cells can be removed for incubation or testing outside the system, before being reintroduced to the patient. For those embodiments in which cells treated for customization are removed from the system, it is preferred that the treated cells or a portion of them are returned to the patient within hours, e.g., 1 hour or less, two hours or less, three hours or less, four hours or less, five hours or less, six hours or less, seven hours or less, eight hours or less, nine hours or less, ten hours or less, twelve hours or less, fourteen hours or less, sixteen hours or less, eighteen hours or less, twenty hours or less, twenty-two hours or less, or twenty-four hours or less.

Cell customization or modification approaches commonly require expansion of cells in culture either before or after a cell modifying or customizing agent, e.g., a nucleic acid or genetic construct, is introduced. Such approaches can also involve cell selection to isolate or enrich for cells that have been successfully modified. The systems and methods described herein generally obviate the need for such expansion or selection, instead using the patient's own body as an incubator to permit, e.g., expression of a therapeutic product, or to permit the customized cells to express a beneficial phenotype or activity. The patient's own body can also permit the expansion, maturation, and/or differentiation of the customized cells to result in therapeutically beneficial effects. Thus, instead of removing cells from the patient and expanding them in culture before treating to modify them, or removing cells from the patient, treating them to modify them, and then expanding them in culture before re-introducing them (or even removing, expanding, treating to modify, then culturing to select for modified cells or to further expand the modified cells), the systems and methods described herein generally bypass the need for steps of expansion or selection for modified cells. That is, in some embodiments, there is no ex vivo expansion of cells involved in the creation of customized or modified cells using a system or method as described herein. Where the patient's own body is used to incubate and/or expand the modified cells, smaller numbers of modified cells (e.g., by a factor of 10 or more, 100 or more or 1000 or more can be re-introduced to the patient than what are most often used in the art when ex vivo expansion techniques are used, e.g., for CAR-T cell therapy. It should be understood that therapeutic effects may not be as rapidly apparent for the systems and methods described herein relative to the effect seen when a bolus of ex vivo-expanded cells is introduced to a patient, but it should also be considered that from start-to-finish (i.e., from introduction of a patient's cells to the system via the inlet conduit to re-introduction of cells to the patient and achievement of therapeutic benefit), the time may be similar or even less than that required for a non-closed-loop procedure that involves ex vivo expansion or culturing of the cells.

Typically, generating CAR-T cells requires expansion of cells in culture either before or after a nucleic acid or genetic construct is introduced encoding the CAR. Autologous adoptive cell transfer involves the collection, modification and return of a patient's immune cell. Typically, leukocytes are isolated, usually by density barrier centrifugation, and T lymphocytes are expanded ex vivo using cell culture methods, often relying on the immunomodulatory action of interleukin-2. Once expanded, the cells are administered intravenously to the patient in an activated state. Such cells are referred to as effector T cells. In addition, a combination of anti-CD3 and anti-CD28 antibodies are commonly used as a surrogate for antigen presentation with appropriate co-stimulation cues to promote the proliferation of T cells in culture. Other interleukins can also be used in these cultures, with an overall objective of enhancing the cytolytic function of the expanded T lymphocytes, once re-infused into the autologous subject.

The systems and approaches described herein can also involve one or more steps of cell selection to isolate or enrich for CAR T cells that have been successfully modified. The systems and methods described herein generally obviate the need for such expansion or selection, instead using the patient's own body as an incubator to permit, e.g., expression of the CAR T cells, or to permit the customized CAR T cells to become activated. Thus, instead of removing blood cells from the patient and expanding them in culture before treating to modify them, or removing cells from the patient, treating them to modify them to CAR T cells, and then expanding them in culture before re-introducing them (or even removing, expanding, treating to modify, then culturing to select for CAR T cells or to further expand the CAR T cells), the systems and methods described herein generally bypass the need for steps of expansion or selection. That is, in some embodiments, there is no ex vivo expansion of cells involved in the creation of CAR T cells using a system or method as described herein. Where the patient's own body is used to incubate and/or expand the modified cells, smaller numbers of CAR T cells (e.g., by a factor of 10 or more, 100 or more or 1000 or more can be re-introduced to the patient than what are most often used in the art when ex vivo expansion techniques are used. It should be understood that therapeutic effects may not be as rapidly apparent for the systems and methods described herein relative to the effect seen when a bolus of ex vivo-expanded CAR T cells is introduced to a patient, but it should also be considered that from start-to-finish (i.e., from introduction of a patient's blood cells to the system via the inlet conduit to re-introduction of cells to the patient and achievement of therapeutic benefit), the time may be similar or even less than that required for a non-closed-loop procedure that involves ex vivo expansion or culturing of the cells.

It should be understood that, while not always explicitly depicted in the diagrams provided herein, the modular bedside systems described herein use anticoagulant agents, such as heparin, that are pumped and coated throughout the components of the system to prevent coagulation of the blood. Thus, the modular systems described herein can comprise an anticoagulant bag or reservoir coupled to an anticoagulant pump (e.g., a peristaltic pump) and appropriate conduit or tubing connected, for example, to deliver anticoagulant to the blood as it enters and flows through the modular systems.

It also should be understood that, the term "module," as used herein, refers to system components that work together to achieve a functional outcome. In other words, components of a given "module" may or may not be in physical proximity and/or contact with each other, but, rather, are in "functional proximity," such that together they achieve one or more defined outcomes. For example, a cell separation module (200) can comprise a centrifuge bowl, as well as a filtration chamber, in some embodiments, such that following centrifugation, nucleated blood cells then undergo one or more filtration steps in the filtration chamber. How these individual components are connected is dependent upon a variety of factors, but the fact that these components work functionally together to achieve certain outcomes, i.e., prepare cells for the cell customization module, indicates that they are part of the same module, regardless of how they are connected physically.

The various modules, units, and components of the system are described further herein below.

Cell Separation Module

One component of the "modular bedside systems" described herein, including that for generating CAR T cells, is the "cell separation module" (200). During use of the systems described herein, a patient is coupled to the system in a closed loop fashion, with an inlet conduit coupled or connected to the patient to provide blood as input to the system (as shown in the exemplary embodiment in FIG. 1). The inlet conduit receives blood directly from the circulation of the patient, from where it then enters the cell separation module. The cell separation module is designed, at a minimum, to perform collection of nucleated cells present in the blood, including, in some embodiments, cell separation followed by one or more enrichment steps, as needed, preferably as part of a continuous flow system. At a minimum, the cell separation module allows for "leukapheresis" of the bulk mononuclear cells present in the blood, namely the separation and collection of leukocytes (WBC) from plasma and red blood cells.

The cell separation module (200) can separate the cells on the basis of size, shape, granularity, buoyancy, density or any combination thereof. Mechanisms for cell separation can include centrifugal force, filtration, elutriation, sonic, or acoustic properties. For example, an apheresis device uses centrifugal force to separate blood fractions. In various embodiments, the cell separation module is interfaced with a detector or detectors capable of detecting one or more properties or parameters of a separated cell population. The detector can detect, as non-limiting examples, cell number, cell size, granularity, or concentration, e.g., via optical or other means, fluorescence, e.g., from a labeled antibody, pH, ionic strength, density, dye exclusion, or other parameters.

In some embodiments, the cell separation module (200) comprises a cell separator (1200) such as an apheresis device. Non-limiting examples of currently used apheresis devices include, for example: COBE® Spectra, TRIMA®, and SPECTRA OPTIA® systems (all marketed by Gambro BCT) and the AMICUS™ and CS-3000+™ (marketed by Fenwal/Baxter) devices. Systems or devices used for cell enrichment and purification purposes include, for example, the BAXTER ISOLEX 300I™ and the Miltenyi CLINI-MACS™, which enrich PBPC (peripheral blood progenitor cells) based on a specific ligand (CD34, both devices and CD133 Miltenyi) on the cells' surface. Other stand-alone devices, such as the Gambro COBE 2991™ Blood Cell Processor or the Fresenius Kabi Lovo™ or Baxter CYTO-MATE™ Cell Washing System are often used to wash, concentrate, or place cells into appropriate growth or infusion medium. Devices of this kind can be adapted for or integrated into a system as described herein for bedside customization of nucleated blood cells.

In some embodiments, the cell separation module (200) can comprise a centrifuge for processing blood cells and separating blood into its component parts using centrifugal forces. For example, in some embodiments, the cell separation module uses a centrifuge bowl, such as, for example, a Latham bowl, as shown in U.S. Pat. No. 4,303,193, which is incorporated herein by reference in its entirety, and separates blood into red blood cells and "buffy coat". The Latham bowl is a blood component separator that has been used for medical leukapheresis, as well as in medical therapies, such as extracorporeal photopheresis (ECP). For example, U.S. Pat. No. 5,984,887 provides descriptions of extracorporeal photopheresis and its method of cell separation and centrifugation, and is incorporated herein by reference in its entirety.

In other embodiments, the cell separation module (200) can use magnetic systems and methods such as those described in US20180010087A1, the contents of which are herein incorporated by reference in their entirety. For example, in some embodiments, an integrated cell processing instrument can be used comprising at least one magnet unit for a magnetic separation chamber, at least one drive for a centrifuge/culture chamber, and various pinch valves arranged such that different arrangements of a tubing set can be mounted onto the instrument. The magnetic separation chamber, the centrifuge/culture chamber and the tubing set can be single-use or disposable units. A cell separation module of this design, and others described herein, can comprise a user interface with integrated monitor and/or computer processor for storing and performing different cell processing operations.

The cell separation module (200) can use, in some embodiments, methods and devices such as those described in WO2017214196A1, the contents of which are herein incorporated by reference in their entirety. More specifically, the systems and methods described herein can use devices and units that accurately direct specific volumes of fluid and/or components present in the whole blood to a desired container in user-specified amounts, so as to allow for the generation of user-defined compositions containing desired volumes of fluid, at desired flow rates and/or containing desired cellular components. Moreover, rather than rely on a set preprogramed routine, some alternatives allow for the dynamic or manual adjustment of the time intervals that particular valves open or close or remain opened or closed so as to allow for incremental partition of components present in an unrefined sample and the direction of specified flows of these components during centrifugation into one or more collection containers, which allows the user to generate a unique mixture of components from whole blood, at desired volumes and/or viscosities. For example, a microcontroller or other circuitry can be used to control a series of short fluid transfers within the cell separation module. The flow rate in the module can be used by the microcontroller to dynamically adjust the valve fluid transfer time period such that a desired amount of fluid comprising the target cell population, or population from which the target cell population will be enriched, is captured as quickly as possible without under- or overshooting a preset target cell volume. For example, in some embodiments, an integrated cell processing instrument can be used comprising at least one elutriation unit to be used as a separation chamber, at least one drive for a centrifuge/culture chamber, and various pinch valves arranged such that different arrangements of a tubing set can be mounted onto the instrument. The elutriation separation chamber can be used to enrich cell populations based on differential buoyant densities and sizes. For more finely purification of specific cell populations the use of antibodies to cell surface proteins attached to elements that would alter the buoyancy of the cells is anticipated. This could be used to either negatively or positively select various cell subsets.

Filters, filtering systems, methods, and devices, particularly those adapted for apheresis of cellular bodies, can also be components of a cell separation module (200) as described herein. A "filter" is a structure that comprises one or more pores or slots of particular dimensions (that can be within a particular range), that allow the passage of some sample components but not others from one side of the filter to the other, based on the size, shape, and/or deformability of the components. A filter can be made of any suitable material, such as metal, ceramics, glass, silicon, plastics, polymers, fibers (such as paper or fabric), etc. that prevents passage of insoluble components. A "filtration unit" is a filtration chamber and the associated inlets, valves, and conduits that allow sample and solutions to be introduced into the filtration chamber and sample components to be removed from the filtration chamber. A filtration unit optionally also comprises a loading reservoir, in some embodiments. Non-limiting examples of filters and filtration chambers suitable for use in the systems and methods described herein can be found in US 2014/0008210A1, the contents of which are incorporated by reference in their entirety.

In some embodiments, a filtration chamber used in the cell separation module (200) (and/or any other module of the systems described herein) is a chamber that comprises or engages at least one microfabricated filter enclosed in a housing. The surface of the filter and/or the inner surface of the housing can be modified by vapor deposition, sublimation, vapor-phase surface reaction, or particle sputtering to produce a uniform coating, in some embodiments. A filtration chamber can comprise one or more fluid-impermeable materials, such as but not limited to, metals, polymers, plastics, ceramics, glass, silicon, or silicon dioxide. Preferably, a filtration chamber has a volumetric capacity of from about 0.01 milliliters to about ten liters, more preferably from about 0.2 milliliters to about two liters. In some embodiments of the systems described herein, a filtration chamber can have a volume of from about 1 milliliter to about 80 milliliters.

A filtration chamber used in the systems described herein can comprise or engage any number of filters. Various filter chamber configurations are possible. A filter can be provided as a wall of a chamber, or internal to a chamber, and filters can optionally be provided in tandem for sequential filtering. Where filters are inserted into a chamber, they are inserted to form a tight seal with the walls of a chamber, such that during the filtration operation, fluid flow through the chamber (from one side of a filter to the other) must be through the pores of the filter. A filtration chamber can also optionally have one or more additional ports for the additions of one or more reagents, solutions, or buffers.

In some embodiments, filtration chambers for use with the systems and methods described herein allow for the passage of mature red blood cells (lacking nuclei) through the channels and thus out of the chamber, while not or minimally allowing cells having a greater diameter or shape (for example but not limited to, nucleated cells such as white blood cells and nucleated red blood cells) to exit the chamber. For example, a filtration chamber having a slot width between 2.0 and 4.0 microns would allow the double-discoid-shaped RBCs to go through the slots while primarily retaining the nucleated RBCs and WBCs with diameters or shapes larger than 7 microns.

Filters can include treatment or modifications to the surface of a filter and/or the inner surface of a housing that encloses the filter to improve its filtering efficiency. In some embodiments, the surface treatment produces a uniform coating of the filter and the housing. In some embodiments, one or both surfaces of the filter is treated or coated or modified to increase its filtering efficiency. In some embodiments, one or both surfaces of the filter is treated or modified to reduce the possibility of sample components (such as but not limited to cells) interacting with or adhering to the filter.

A filter and/or filter chamber can be physically or chemically treated, for example, to alter surface properties (e.g., hydrophobic, hydrophilic), and thereby reduce the interaction of sample components with the filter and/or housing surface, in some embodiments. For example, vapor deposition, sublimation, vapor-phase surface reaction, or particle sputtering are some of the methods that can be used to treat or modify the surface of a filter and/or filter chamber. Any suitable vapor deposition methods can be used, e.g., physical vapor deposition, plasma-enhanced chemical vapor deposition, chemical vapor deposition, etc. Suitable materials for physical vapor deposition, chemical vapor deposition, plasma-enhanced chemical vapor deposition or particle sputtering may include, but are not limited to, a metal nitride or a metal halide, such as titanium nitride, silicon nitride, zinc nitride, indium nitride, boron nitride, Parylene or a derivative thereof, such as Parylene, Parylene-N, Parylene-D, Parylene AF-4, Parylene SF, and Parylene HT, Polytetrafluoroethylene (PTFE) or Teflon-AF can also be used for chemical vapor deposition.

In some embodiments, traveling-wave dielectrophoretic forces can be generated by electrodes built onto a chip that is part of a filtration chamber, and can be used to move sample components such as cells away from a filter. In this case, the microelectrodes are fabricated onto the filter surfaces and the electrodes are arranged so that the traveling wave dielectrophoresis can cause the sample components such as cells to move on the electrode plane or the filter surface through which the filtration process occur. A full description of traveling wave dielectrophoresis is provided in U.S. application Ser. No. 09/679,024 herein incorporated by reference in its entirety.

A filtration chamber can also comprise a component that comprises electromagnetic elements. Such electromagnetic elements can be used for the capture of sample components before or, preferably, after, filtering of the sample. Sample components can be captured after being bound to magnetic beads. The captured sample components can be either undesirable components to be retained in the chamber after the sample containing desirable components has already been removed from the chamber, or the captured sample components can be desirable components captured in the chamber after filtration.

An acoustic force chip can engage or be part of a filtration chamber, or one or more acoustic elements can be provided on one or more walls of a filtration chamber, in some embodiments. Mixing of a sample by the activation of the acoustic force chip can occur during the filtration procedure. Preferably, a power supply is used to transmit an electric signal to the acoustic elements of one or more acoustic chips or one or more acoustic elements on one or more walls or a chamber. One or more acoustic elements can be active continuously throughout the filtration procedure, or can be activated for intervals (pulses) during the filtration procedure.

In some embodiments of the modules described herein, a cylindrical filter that employs a thin micro-machined porous filter membrane with a regular array of pores that can reliably pass blood while trapping cells from the blood can be used. See, for example, US20180043084A1, the contents of which are herein incorporated by reference in their entirety.

Enrichment Unit

The cell separation module (200), at a minimum, collects bulk nucleated blood cells from the patient blood received through the inlet conduit and allows for leukapheresis, i.e., the separation and collection of leukocytes (WBC) from plasma and red blood cells.

In addition, the cell separation module (200) can, in some embodiments, subsequently enrich for one or more target cell lymphocyte populations from the bulk nucleated blood cells. Accordingly, techniques and methods can be integrated into, or work functionally with, the cell separation modules described herein, to further fractionate cell populations or to select for a particular target cell type or class, e.g., all lymphocytes, or all T cells, among others. Such techniques include but are not limited to magnetic separation, filtration, immunoaffinity separation, gravitation separation, density gradient separation, elutriation, and any combinations thereof. The cell separation module can employ any of these or other methods known in the art for further enriching for and/or obtaining a target population of nucleated blood cells from a patient. For example, binding to one or more selective or affinity agents, such as antibodies attached to degradable buoyant beads or magnetic beads or microbubbles, can be used to enrich for a particular target cell type or class, following the cell separation.

Thus, in some embodiments, the cell separation module (200) can further comprise an enrichment unit (1100) that enriches for one or more cell populations for various purposes, including providing an enriched target cell population(s) for use in the cell customization module, e.g., where a CAR construct is introduced. Target cell populations refer to cells that are enriched from peripheral blood following bulk nucleated cell collection in the cell separation module. The terms "enriching" or "enriched" are used interchangeably herein and mean that the yield (fraction) of cells of one type, such as, for example, T cells, for use in the systems and methods described herein, is increased by at least 5 fold, at least 10-fold, at least 20-fold, at least 30-fold, at least 40-fold, at least 50-fold, at least 60-fold, at least 70-fold, at least 80-fold, at least 90-fold, at least 100-fold or more over the fraction of cells of that type in the starting sample of bulk nucleated cells. The enrichment of the target cell population can be to enrich to a percentage purity required for the cell customization module and/or eliminate a particular target cell or cell types from the population prior to cell customization.

Non-limiting examples of cell types that can be enriched from a leukapheresis bulk product include B lymphocytes, T lymphocytes, CD4 and CD8 T lymphocytes, dendritic cells, monocytes, natural killer (NK) cells, NKT cells, T-regulatory cells, CD4 T-helper cells, CD8 cytotoxic T lymphocytes (CTLs), NKT cells, neutrophils, basophils, eosinophils, megakaryocytes, hematopoietic stem cells (HSCs), hematopoietic progenitor cells (HPCs), lymphokine-activated killer cells (LAKs), tumor infiltrating lymphocytes (TILs), mesenchymal stem cells, mast cells, subsets of such cells, and combinations thereof. While the systems described herein will most often be applicable to the modification of nucleated blood cells, it is contemplated that in some embodiments, red blood cells (RBCs) or erythrocytes, can be modified using the systems described herein, e.g., to load them with a drug or therapeutically useful biologic agent. In such instances, it is a straightforward matter to direct the RBCs into the cell customization module instead of the nucleated cells.

In some embodiments of the systems and methods described herein, enrichment of the target cell populations can be by chemical or physical means, e.g., capture, and the individual cells of the target cell populations are said to be isolated from the bulk blood cell population. The enrichment procedure in an enrichment unit (1100) incorporated, e.g., within or as part of the cell separation module (200), can employ one or more methods known in the art including, without limitation, antigen capture, e.g., on filters, beads or magnetics, fluorescence-activated cell sorting, microfluidics, solid support affinity, acoustics, bioluminescence, antibody tagging, or enzyme substrate. Suitable solid supports include particles including, without limitation, ferromagnetic and density modified particles. Solid supports and such supports comprising affinity molecules, such as antibody domains that bind a given cell-surface marker can be obtained, for instance from Miltenyi Biotec and Dynal. Methods that can be used for the release of the captured cells include, but are not limited to, i) competition with excess ligand, ii) enzymatic digestion, iii) change in pH, iv) change in ionic strength, v) removal of magnetic field, and/or vi) physical agitation.

Markers or determinants specific for target cell populations, e.g., T cell populations, can be used to isolate or enrich for these cells. A "marker," as used herein, describes the characteristics and/or phenotype of a cell. Markers can be used for selection of cells comprising characteristics of interest. Markers can vary with specific cells. Markers can be, for example, molecules expressed by or on a given cell type, morphological, functional or biochemical (enzymatic). Preferably, such markers are proteins, and more preferably, proteins that possess an epitope for antibodies or other binding molecules available in the art. Examples of morphological characteristics or traits include, but are not limited to, shape, size, appearance (e.g., smooth, translucent), density, granularity, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art.

A cell separation module (200) can include an enrichment unit (1100) that uses or exploits one or more "cell-surface determinants" or "cell-surface markers" for enrichment of a target cell population(s). A "cell-surface marker" refers to any molecule that is expressed on the surface of a cell. Cell-surface expression usually requires that a molecule possesses a transmembrane domain. Many naturally occurring cell-surface markers are termed "CD" or "cluster of differentiation" molecules. Cell-surface markers often provide antigenic determinants to which antibodies can bind. Non-limiting examples of human cell-surface markers useful for the systems and methods described herein are provided in Table 1.

TABLE 1

| | |
|---|---|
| B Cells | CD19, CD20 |
| T Cells | CD3, CD56(−), CD4, CD8 |
| Activated and/or Regulatory T Cells | CD25, CD69 |
| Dendritic Cells | CD1c, CD83, CD141, CD209, MHC II, CD11c |
| Plasmacytoid Dendritic Cells | CD123, CD303, CD304 |
| Platelets (resting) | CD42b, CD41, CD61 |
| Platelets (activated) | CD62P |
| Natural Killer Cells | CD3(−), CD16, CD56 |
| Hematopoietic Stem or Progenitor Cells | CD34, CD90, CD135 |
| Macrophage | CD11b, CD68, CD163, CD33 |
| Monocyte | CD14, CD16, CD64 |
| Plasma Cells | CD138 |
| Red Blood Cells | CD235a |

TABLE 1-continued

| | |
|---|---|
| Neutrophils | CD15, CD16, CD49d(−) |
| Basophils | 2D7 antigen, CD117(−), CD123, CD203c, FcεRIα |
| Eosinophils | CD11b, CD193, EMR1, Siglec-8 |

A cell can be designated "positive" or "negative" for any cell-surface marker, and both such designations are useful in the systems and methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing analysis, such as fluorescence measurements, of such a contacted cell to determine whether the antibody is bound the cell. It is to be understood that while a cell can express messenger RNA for a cell-surface marker, in order to be considered positive for the systems and methods described herein, the cell must express the marker on its surface. Similarly, a cell is considered "negative" for a cell-surface marker if it does not express the marker on its cell-surface in amounts sufficient to be detected using methods known to those of skill in the art, such as contacting a cell with an antibody that binds specifically to that marker and subsequently performing analysis of such a contacted cell to determine whether the antibody is bound the cell. In some embodiments, where agents specific for cell-surface lineage markers are used, the agents can all comprise the same label or tag, such as fluorescent tag, and thus all cells positive for that label or tag can be excluded or removed, to leave uncontacted cells comprising the target cell population for customization using the systems and methods described herein.

Accordingly, as defined herein, an "agent specific for a cell-surface marker" refers to an agent that can selectively react with or bind to that cell-surface marker, but has little or no detectable reactivity to another cell-surface marker or antigen. Thus, agents specific for cell-surface markers recognize unique structural features of the markers. In some embodiments, an agent specific for a cell-surface marker binds to the cell-surface marker, but does not cause initiation of downstream signaling events mediated by that cell-surface marker, for example, a non-activating antibody. Agents specific for cell-surface markers include, but are not limited to, antibodies or antigen-binding fragments thereof, natural or recombinant ligands, small molecules; nucleic acids and nucleic acid analogues; aptamers; intrabodies; and other proteins or peptides.

For use with the systems and methods described herein, preferred agents specific for cell-surface markers are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single $V_L$ or $V_H$ antibody domains), Fv fragment, including single chain Fv fragment (scFv), Fab fragment, and F(ab')2 fragment. Methods for the construction of such antibody molecules are well known in the art. Antigen-binding fragments can be produced by recombinant DNA techniques or by enzymatic or chemical cleavage of intact antibodies. Antibodies or antigen-binding fragments are available commercially from vendors such as R&D Systems, BD Biosciences, e-Biosciences, BioLegend, and Miltenyi, or can be raised against these cell-surface markers by methods known to those skilled in the art.

In some embodiments, an agent specific for a cell-surface molecule, such as an antibody or antigen-binding fragment, is labeled with a tag to facilitate the selection or isolation of the hematopoietic cell populations. The terms "label" or "tag", as used herein, refer to a composition capable of producing a detectable signal indicative of the presence of a target, such as, the presence of a specific cell-surface marker in a biological sample. Suitable labels include particles and beads, such as magnetic beads or particles or nanoparticles, radioisotopes, nucleotide chromophores, enzymes, substrates, chemiluminescent moieties, magnetic particles, bioluminescent moieties, fluorescent molecules, and the like. As such, a label is any composition detectable by magnetic, spectroscopic, photochemical, biochemical, immunochemical, electrical, optical, or chemical means used with the systems and methods described herein. Proteins or antibodies can also be labeled with a detectable epitope tag, such as epitopes derived from c-Myc, HA, VSV-G, HSV, FLAG, V5, or HIS, which can in turn be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the systems and methods described herein include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5, Cy7, nanoparticles, or quantum dots. In one embodiment, a detector as described herein can detect fluorescence, e.g., from a labeled antibody or other affinity agent bound to a fraction or population of cells, or from a fluorescently labeled reagent introduced to cells as a surrogate marker for modification. This can encompass, for example, flow cytometric detection. However, the throughput of flow cytometry is not generally optimal to provide T cells for CAR T cell generation, as described herein, or to purify such CAR T cells. Thus, in some embodiments, the fluorescence detection is not flow cytometric detection. Instead, fluorescent detection can be used, for example, to detect the amount of a marker present in or on a population of cells in a sampling, holding or incubation unit associated with one or more modules described herein. In such embodiments, the detector can, for example, detect the amount of the label in or associated with a given population, such that, for example, when a threshold amount indicative of sufficient numbers of customized cells for a given therapeutic approach is detected, the processor directs the population back to the patient. For example, the detector can detect cell number or the number of CD3 cells or the CD4:CD8 ratio. In this manner, even if there is low efficiency of customization, e.g., CAR T cells generated, the system can be effectively monitored such that a clinician or operator knows when a number of (e.g., CAR T) cells sufficient for a desired therapeutic effect have been generated/customized. This principle is adaptable to other types of detection as known in the art or described herein.

In some embodiments, a cell separation module (200) comprises an enrichment unit (1100) that uses magnetic beads coated with antibodies against one or more specific cell-surface antigens to perform one or more selection steps on the nucleated blood cells following cell separation of whole blood. This causes the cells in the enrichment unit expressing this antigen to attach to the magnetic beads. When exposed to a strong magnetic field, such as a magnet present within the enrichment unit or other physical location of the cell separation module, the cells attached to the beads (expressing the cell-surface marker) stay on the column or sample tube, while other cells (not expressing the cell-surface marker) flow through or remain in suspension. Using this method, cells can be selected positively or negatively, or using a combination of positive and negative selection, with respect to the particular cell-surface markers. In some embodiments, cells are still coupled with the microbead-bound antibodies when they reenter the patient through the outlet conduit.

Thus, in some embodiments, the enrichment unit (1100) uses negative selection and comprises a reagent, such as an antibody, that specifically binds a cell-surface determinant on nucleated blood cells other than the subset of target nucleated blood cells entering the cell customization module (e.g., where the CAR T cells are customized and generated), thereby selectively enriching for a/the subset of target nucleated blood cells to be customized in the fraction of unbound cells. In some embodiments, the enrichment unit uses positive selection and comprises a reagent that specifically binds a cell-surface determinant present on the subset of target nucleated blood cells, thereby selectively enriching for the subset of target nucleated blood cells in the bound fraction. For example, where positive selection is used in certain CAR T embodiments, reagents can be used that specifically bind CD4 and CD8. As defined herein, "positive selection" refers to techniques that result in the isolation or enrichment of cells expressing specific cell-surface markers, while "negative selection" refers to techniques that result in the isolation or enrichment of cells not expressing specific cell-surface markers.

During the enrichment step(s) in the cell separation module (200), more than one target cell population can be enriched for. The system can enrich target cell populations in various ways, e.g., the different cell types can be enriched separately in different chambers or areas. The different target cell populations can be processed together (e.g., all returned to the patient or all discarded) or the cell types can be processed separately (e.g., one set returned to the patient, one set discarded, etc.) or variations thereof.

Other methods that can be used to enrich for a target cell population can use methods known in the art or discussed herein, in combination. Thus, capture or selection on the basis of binding to one cell surface antigen can be combined, for example, with negative selection to remove cells expressing another marker, or can be combined with other methods to enrich for a target cell population.

Cell Washing Unit

In various embodiments, a cell washing unit (210) can be integrated with the cell separation module (200), or can be placed temporally and physically downstream of the cell separation module, e.g., between the cell separation module (200) and the cell customization module (400), to remove one or more components of a cell suspension produced by the cell separation module, or in order to place the cells into a medium or solution better conducive to customization (e.g., generating CAR T cells). An optional cell sampling port can be added in line for the sterile removal of sample for analysis. This sampling unit (450A) can be placed after the cell separation (1200) or after the cell washing and enrichment steps (210 and 1100) for purposes of in-line testing and analysis within the system or for external sampling for testing and analysis. A cell washing unit includes a source of cell wash solution, such as a reservoir or bag of wash solution, connected via conduit or tubing to the washing unit. The flow of cell wash solution can be controlled by a valve controlled by the processor. As but one example, cells can be washed in and suspended in an electroporation buffer, when the cell customization module (400) includes an electroporation unit. A cell washing unit can include a centrifugal unit similar to the centrifugal unit in an apheresis device; cells enter the washing unit, are mixed with wash solution introduced from a reservoir or other source of wash solution via conduit connected to the washing unit, and the suspension is spun to concentrate cells. One or more rounds of cell washing and re-suspension can be performed before the cells are introduced to the cell customization module, or a continuous process can be used that introduces new solution to the cells as they are spun. As an alternative, or in addition, the cell customization module (400) can include a cell washing unit (410). As yet another alternative, the cell washing unit can be separate from either the cell separation module or the cell customization module—in such an alternative, the cell washing unit (310) can be connected between the cell separation module and the cell customization module. A cell washing unit can be interfaced with a detector that senses one or more properties of the cells or cell suspension, e.g., cell number, solution density, solution pH, solution ionic strength, etc. A cell washing unit is generally also interfaced with the processor that controls the function of the various modules and the system as described herein.

Thus, the cell separation module (200), as described herein, collects a population of nucleated blood cells from input whole blood, for delivery, either directly, or via an enrichment unit (1100) and/or cell washing unit, to the cell customization module (400). The cell separation module can enrich for one or more target cell populations (e.g., such as lymphocytes or T cells) from the bulk nucleated blood cells, and can have an operator interface for receiving inputs and providing outputs to an operator.

Cell Customization or Modifying Agents

Once separated from whole blood, the nucleated blood cell population or enriched target cell population can be modified and/or customized using any method known in the art, including, without limitation, activation, expansion, induction of apoptosis, genetic manipulation, induction of antigen-specificity, etc. This can be achieved, for example, by the addition of cytokines, cross-linking specific receptors, addition of antigen, introduction of nucleic acid molecules (DNA, RNA, and/or modified versions thereof), protein agents, addition of drugs or small molecules, or any combination thereof.

A variety of cell customization agents can be applied to the target cell population in the different embodiments of the cell customization modules described herein. Cell customization agents, as used herein, include any molecule or compound capable of exerting a desired effect on a cell found in the blood. Non-limiting examples of cell customization agents include, but are not limited to, therapeutic nucleic acid molecules; peptide, protein, and polypeptide therapeutic agents, including, but not limited to polyclonal antibodies, monoclonal antibodies, antibody fragments; humanized antibodies, recombinant antibodies, recombinant human antibodies, fully human antibodies, cytokines, growth factors, apoptotic factors, differentiation-inducing factors, cell surface receptors and their ligands, and hormones; and small molecule agents, including small organic molecules or compounds. Non-limiting examples of classes of small molecule agents useful with the systems and methods described herein include anti-inflammatory compounds, antibiotics, antipyretics, vasodilators, anti-angiogenics, cytovascular agents, signal transduction inhibitors, and any combination thereof.

In some embodiments, the cell customization agent is an oncology drug, which may also be referred to as an anti-tumor drug, an anti-cancer drug, a tumor drug, an antineoplastic agent, a chemotherapeutic drug, or the like. In such embodiments, it is contemplated that systemic toxicity of chemotherapeutic drugs useful for, e.g., treatment of blood cancers such as leukemias, lymphomas or myelomas can be mitigated by administering the drug to nucleated blood cells, which will include the cancer cells, separated from whole blood, in a bedside, closed-loop system as described herein. Examples of oncology drugs that can be used in this manner include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs are ellipticin and ellipticin analogs or derivatives, epothilones, intracellular kinase inhibitors and camptothecins.

Cell customization agents can be therapeutically active themselves or they can be prodrugs, which become active upon further modification.

Therapeutic or cell-customizing or modifying nucleic acids include, but are not limited to, nucleic acids that encode one or more peptides or polypeptides of interest, such as mRNAs, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and aptamers.

SLIPSTREAM™ is another technique or platform/module useable in the presently contemplated systems. In such a technique or platform deep-primed T Cells are produced using an apheresis-based technique such as those described in, e.g., WO2019010222, WO2019010219, WO2019-010224, each of which is incorporated herein by reference in its entirety. In a related exemplary embodiment, T Cells and monocytes are isolated. Monocytes are then matured into dendritic cells and used to prime the T cells with multiple tumor-associated antigens. In such embodiments, a blend of CD4 and CD8 cells is produced. The T cells then are expanded to produce several billion tumor-targeting-primed, high-viability CD4+ and CD8+ T cells. An agent such as an immune-stimulatory drug, is then tethered to the surface of the antigen-primed T cells, which are then returned to the patient.

Gene editing tools are included in the available cell customizations, including gene alterations, knockouts, or other changes to a cell's DNA, contemplated herein. For example, zinc finger nucleases (ZFN), transcription activator-like effector nucleases (TALEN), and Clustered Regularly Interspaced Short Palindromic Repeats (CRISPR) and CRISPR-associated (Cas) systems are frequently included gene editing tools included as cell customization options according to the methods, systems, and kits contemplated herein. See, e.g., Urnov et al. Nat Rev Genet. 2010; 11(9): 636-646; Kim et al., Genome Res. 2009; 19(7):1279-1288; Bogdanove & Voytas, Science 2011; 333(6051):1843-1846; Hockemeyer, Nat Biotechnol. 2011; 29(8):731-734; Kim et al., Nat Biotechnol. 2013; 31(3):251-258; Cong et al., Science 2013; 339(6121):819-823; Cho et al., Nat Biotechnol. 2013; 31(3):230-232; Genovese et al., Nature 2014; 510 (7504):235-240; Sebastiano et al., Stem Cells 2011; 29(11): 1717-1726, each of which is incorporated herein by reference in its entirety. Gene editing can be performed, for example, using a nuclease, including CRISPR associated proteins (Cas proteins, e.g., Cas9), ZFN, TALEN, and maganucleases.

With specific regard to CRISPR-Cas systems, a variety of reagents, methods techniques, and modules are utilized according to the present disclosure. For example, DNA breaks can be generated using a CRISPR-cas system, e.g., a type II CRISPR/cas system. Cas9 is an exemplary Cas enzyme used according to such methods disclosed, which catalyzes DNA cleavage. Enzymatic action by Cas9 can generate double stranded breaks at target site sequences which hybridize to at or about 20 nucleotides of a guide sequence and that have a protospacer-adjacent motif following the 20 nucleotides of the target sequence. A vector can be operably linked to an enzyme-coding sequence encoding a CRISPR enzyme, such as a Cas protein. Non-limiting examples of Cas proteins include Cas1, Cas1B, Cas2, Cas3, Cas4, Cas5, Cas5d, Cas5t, Cas5h, Cas5a, Cash, Cas7, Cas8, Cas9 (also known as Csn1 or Csx12), Cas10, Cmr1, Cmr3, Cmr4, Cmr5, Cmr6, Csa1, Csa2, Csa3, Csa4, Csa5, CsaX, Csb1, Csb2, Csb3, Csc1, Csc2, Csd1, Csd2, Cse1, Cse2, Cse3, Cse4, Cse5e, Csf1, Csf2, Csn1, Csn2, Csm1, Csm2, Csm3, Csm4, Csm5, Csm6, Csx17, Csx14, Csx10, Csx16, Csx3, Csx1, Csx1S, CsO, Csf4, Cst1, Cst2, Csh1, Csh2, Csy1, Csy2, Csy3, Csy4, including homologues or modified versions thereof. For example, a CRISPR enzyme can cleave of one or both strands at or around at least about 1, 2, 3, 4, 5, 6, 7, 8, 9, 10, 15, 20, 25, 50, 100, 200, 500, or more base pairs from a predetermined (e.g., first or last) nucleotide of a specific.

A vector that encodes a CRISPR enzyme comprising one or more nuclear localization sequences can be used. A CRISPR enzyme can comprise the nuclear localization sequences at or near the ammo-terminus, about or within a predetermined distance at or near the carboxy-terminus. CRISPR enzymes contemplated herein are non-limited.

The contemplated CRISPR/Cas systems can be used according to the contemplated customizations to perform site specific insertion or removals of sequence. For example, a nick on an insertion site in the genome can be made by CRISPR/cas to facilitate the insertion of a transgene at the insertion site. Alternatively, specific genes may be removed from the DNA of the cell. In often included embodiments, the presently contemplated cell customizations include methods of modulating the expression and/or activity of one or more target nucleic acid sequences in one or more cells by introducing into the cell one or more ribonucleic acid (RNA) sequences that comprise a portion that is complementary to each of the one or more target nucleic acid sequences and comprise a binding site for a CRISPR associated (Cas) protein; (ii) a Cas nucleic acid sequence or a variant thereof that encodes the Cas protein that targets but does not cleave the target nucleic acid sequence; and (iii) an effector domain. Such customizations may also include maintaining a target cell under conditions where these RNA sequences hybridize to a portion of the target nucleic acid sequences, the Cas protein binds to the RNA sequences and the effector domain modulates the expression and/or activity of the target nucleic acid, thereby modulating the expression and/or activity of the one or more target nucleic acid sequences in the cell. Exemplary CRISPR/Cas systems, methods, reagents, devices and modules contemplated herein are described, for example, in U.S. Pat. No. 10,253, 316; U.S. Patent App. Pub. Nos. 20160046961, 2016-0298096A1, 201662427325, 20170204407; PCT Application Pub No. WO2019067910A1, each of which is incorporated herein by reference in its entirety.

Regarding CAR T cell generation, it should be understood that substantially any CAR polypeptide that can be used in conventional CAR T therapy can be employed or introduced in the systems and methods described herein. That is, the specifics of the CAR are not generally critical to the invention described herein. That said, for the avoidance of doubt, the following describes options and considerations for a range of CAR constructs that can be used with the systems and methods described herein.

Typically, in adoptive immunotherapy, the patient's circulating lymphocytes, or tumor infiltrated lymphocytes, are isolated in vitro, activated by lymphokines, such as IL-2 or transduced with genes for tumor targeting, and re-administered. To achieve this, one would administer to an animal, or human patient, an immunologically effective amount of activated lymphocytes genetically modified to express a tumor-specific chimeric antigen receptor gene as described herein. The activated, tumor-targeted lymphocytes are preferably the patient's own cells that were earlier isolated from a blood or tumor sample and activated and expanded in vitro.

In contrast, as described herein, once separated from whole blood, the nucleated blood cell population or enriched target cell population can undergo one or more steps whereby patient-specific CAR T cells are generated. This can be achieved by any method known in the art, for example, introduction of nucleic acid molecules (DNA, RNA, and/or modified versions thereof) encoding the CAR, along with, in some embodiments, addition of cytokines, growth factors, or the like, and/or cross-linking specific receptors on the T cells, or any combination thereof.

The term "chimeric antigen receptor" as used herein is defined as a cell-surface receptor comprising an extracellular ligand-binding or antigen-binding domain, a transmembrane domain, and a cytoplasmic co-stimulatory signaling domain in a combination that is not naturally found together on a single protein. This particularly includes receptors wherein the extracellular domain and the cytoplasmic domain are not naturally found together on a single receptor protein. Further, the chimeric antigen receptor is different from the TCR expressed in the native T cell lymphocyte. As described in U.S. Pat. Nos. 5,359,046, 5,686,281 and 6,103,521, the contents of which are herein incorporated by reference in their entireties, the extracellular domain can be obtained from any of the wide variety of extracellular domains or secreted proteins associated with ligand binding and/or signal transduction. The extracellular domain can be part of a protein which is monomeric, homodimeric, heterodimeric, or associated with a larger number of proteins in a non-covalent complex.

In particular, in preferred embodiments, the extracellular domain can comprise an Ig heavy chain which can, in turn, be covalently associated with Ig light chain by virtue of the presence of CH1 and hinge regions, or can become covalently associated with other Ig heavy/light chain complexes by virtue of the presence of hinge, CH2, and CH3 domains. In the latter case, the heavy/light chain complex that becomes joined to the chimeric construct can constitute an antibody with a specificity distinct from the antibody specificity of the chimeric construct. Depending on the function of the antibody, the desired structure and the signal transduction, the entire chain can be used or a truncated chain can be used, where all or a part of the CH1, CH2, or CH3 domains can be removed or all or part of the hinge region can be removed.

As described herein, in some embodiments, the extracellular domains of CARS are derived from immunoglobulins. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g., Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former, but not the latter, is lost in the presence of denaturing solvents.

When an anti-tumor chimeric antigen receptor is utilized, the tumor can be of any kind as long as it has a cell surface antigen that can be recognized by the chimeric receptor. In some embodiments of the aspects described herein, the chimeric antigen receptor can be for any cancer for which a specific monoclonal antibody exists or is capable of being generated. For example, cancers such as neuroblastoma, small cell lung cancer, melanoma, ovarian cancer, renal cell carcinoma, colon cancer, Hodgkin's lymphoma, and acute lymphoblastic leukemia (e.g., childhood acute lymphoblastic leukemia) have antigens known to be able to be targeted by the chimeric antigen receptors. The systems and methods described herein can be used in immunotherapy in the treatment of cancer, such as the treatment of lung cancer, melanoma, breast cancer, prostate cancer, colon cancer, renal cell carcinoma, ovarian cancer, neuroblastoma, rhabdomyosarcoma, leukemia and lymphoma. The systems and methods described herein can be utilized in conjunction with other types of therapy for cancer, such as chemotherapy, surgery, radiation, gene therapy, and so forth, as described hereinafter.

Non-limiting examples of tumor antigens that can be targeted by the extracellular domain of a CAR can be found in Table 1.

TABLE 1

| Non-limiting Examples of Tumor Antigens for Targeting by CAR T Cells | |
|---|---|
| Antigen | Reference Tumor antigens |
| CD19 | GenBank Acc. No. NM_001178098; NP_001171569; UniProt P15391 (The Lancet, Early Online Publication, 13 Oct. 2014 doi: 10.1016/S0140-6736(14)601403-3). |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Grob, et al. (2005) Proc. Natl. Acad. Sci. USA 102; 6461-6466; GenBank Acc. Nos. NM_000247; BC_016929; AY750850; NM_005931. |

TABLE 1-continued

Non-limiting Examples of Tumor Antigens for Targeting by CAR T Cells

| Antigen | Reference Tumor antigens |
|---|---|
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484 Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |

TABLE 1-continued

Non-limiting Examples of Tumor Antigens for Targeting by CAR T Cells

| Antigen | Reference Tumor antigens |
|---|---|
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE: HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; AS9T; Q61H. K-RAS; H-RAS; N-RAS. | GenBank Acc. Nos. P01112; P01116; MS4969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol, Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastroenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGB-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |

TABLE 1-continued

Non-limiting Examples of Tumor Antigens for Targeting by CAR T Cells

| Antigen | Reference Tumor antigens |
|---|---|
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL, AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799: U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. application Ser. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Pat. Publication No. 2005/0281783 A1; Genbank Accession No. NM_004431 (human); Genbank Accession No. |

TABLE 1-continued

Non-limiting Examples of Tumor Antigens for Targeting by CAR T Cells

| Antigen | Reference Tumor antigens |
|---|---|
|  | NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

The transmembrane domain of a CAR can be contributed by the protein contributing the multispecific extracellular inducer clustering domain, the protein contributing the effector function signaling domain, the protein contributing the proliferation signaling portion, or by a totally different protein. For the most part it will be convenient to have the transmembrane domain naturally associated with one of the domains. In some cases it will be desirable to employ the transmembrane domain of the ζ, η, or FcεR1γ chains which contain a cysteine residue capable of disulfide bonding, so that the resulting chimeric protein will be able to form disulfide linked dimers with itself, or with unmodified versions of the ζ, η, or FcεR1γ chains or related proteins. In some embodiments, the transmembrane domain is selected or modified by amino acid substitution to avoid binding of such domains to the transmembrane domains of the same or different surface membrane proteins to minimize interactions with other members of the receptor complex. In other embodiments, the transmembrane domain of ζ, η, or FcεR1γ chains and β, MB1 (Igα), B29 or CD3γ, ζ, or ε, are employed in order to retain physical association with other members of the receptor complex. Examples of suitable transmembrane regions for use in the agents for generating CAR T cells used with the systems and methods described herein include the constant (Fc) regions of immunoglobins, human CD8a, and artificial linkers that serve to move the targeting moiety away from the cell surface for improved access to and binding on target cells. However any transmembrane region sufficient to anchor the CAR in the membrane can be used. Persons of skill are aware of numerous transmembrane regions and the structural elements (such as lipophilic amino acid regions) that produce transmembrane domains in numerous membrane proteins and therefore can select a sequence as necessary without undue experimentation.

The cytoplasmic domain of the chimeric antigen receptors for use with the systems and methods described herein can comprise a signaling domain (e.g., co-stimulatory signaling domain) by itself or combined with any other desired cytoplasmic domain(s) useful in the context of this chimeric receptor type, such as for example, a 4-1BB signaling domain, a CD3ζ signaling domain and/or a CD28 signaling domain. The 4-1BB, CD3ζ and CD28 signaling domains are well characterized, including for example, their use in chimeric receptors. In some embodiments, the cytoplasmic domain of the chimeric receptors can comprise the 4-1BB signaling domain by itself or combined with any other desired cytoplasmic domain(s) useful in the context of this chimeric receptor type. In some embodiments, the extracellular domain comprises a single chain variable domain of a monoclonal antibody, the transmembrane domain comprises the hinge and transmembrane domain of CD8α, and the cytoplasmic domain comprises the signaling domain of CD3ζ and the signaling domain of 4-1BB. The CD8a hinge and transmembrane domain contains 69 amino acids translated from the 207 nucleotides at positions 815-1021 of GenBank Accession No. NM_001768. The CD3ζ signaling domain contains 112 amino acids translated from 339 nucleotides at positions 1022-1360 of GenBank Accession No. NM_000734.

In some embodiments, cell customization agents (e.g., therapeutic or modifying nucleic acids for generating CAR T cells) for use with the systems and methods described herein are nucleic acid molecules, specifically polynucleotides, primary constructs and/or mRNA molecules, that encode one or more polypeptides of interest. The term "nucleic acid," in its broadest sense, includes any compound and/or substance that comprise a polymer of nucleotides. A nucleic acid as used herein will either encode a polypeptide product or modulate the expression (including transcription and/or translation) of one or more gene products. Exemplary nucleic acids or polynucleotides contemplated for use with the systems described herein include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a (3-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Genetic modification for use with the systems and methods described herein can be accomplished by transducing (or otherwise delivering) a cell with a recombinant DNA or RNA construct. For example, genetic modification for introduction of the CAR construct into T cells can be accomplished by transducing (or otherwise delivering) a cell with a recombinant DNA or RNA construct. While typically such constructs are delivered ex vivo using vectors, such as viral vectors, it is preferred that, for use with the systems and methods described herein, agents (e.g., for generating CAR T cells) that are capable of delivering or maintaining nucleic acid in a host cell, do not include viral vectors (e.g., retroviral vectors, lentiviral vectors, adenoviral vectors, or adeno-associated viral vectors), but comprise naked nucleic acids, nucleic acids complexed with polypeptide or other molecules, and nucleic acids immobilized onto solid phase particles. Such procedures and others are deemed to be within the scope of those skilled in the art. One non-limiting example of such a non-viral system that can be used with the systems and methods described herein is the latest generation of Sleeping Beauty (SB) transposon vectors that permit high-level stable gene transfer and sustained transgene expression in multiple primary human somatic cell types, and include optimized transposons and hyperactive SB variants, as described in "Going non-viral: the Sleeping Beauty transposon system breaks on through to the clinical side," CRITICAL REVIEWS IN BIOCHEMISTRY AND MOLECULAR BIOLOGY, 2017, VOL. 52, NO. 4, 355-380; and "The Sleeping Beauty transposon system: a non-viral vector for gene therapy," Hum Mol Genet. 2011 Apr. 15; 20(R1): R14-R20, the contents of each of which are herein incorporated by reference in their entireties.

In some embodiments, the nucleic acid molecule is a messenger RNA (mRNA). As used herein, the term "messenger RNA" (mRNA) refers to any polynucleotide, including, but not limited to a synthetic polynucleotide, which encodes a polypeptide of interest and which is capable of being translated to produce the encoded polypeptide of interest in vitro, in vivo, in situ or ex vivo. Typically, the basic components of an mRNA molecule include at least a coding region, a 5'UTR, a 3'UTR, a 5' cap and a poly-A tail. In some embodiments, synthetic modified RNA molecules, termed herein as "mmRNA," are used. See, for example, US Patent Publication 20180036369, the contents of which are herein incorporated by reference in their entireties. Any of the polynucleotides, primary constructs and mmRNA described herein can be formulated as described in International Application No. PCT/US2012/069610, the contents of which is herein incorporated by reference in its entirety.

Accordingly, in some embodiments, a formulation for use with the systems and methods described herein comprises at least one mmRNA. As a non-limiting example, the formulations can comprise 1, 2, 3, 4 or 5 mmRNA. In some embodiments, the formulation comprises modified mRNA encoding proteins selected from categories such as, but not limited to, biological proteins, antibodies, chimeric antigen receptors, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In some embodiments, the formulation comprises modified mRNA encoding a chimeric antigen receptors targeting an antigen of interest, such as a cancer or tumor antigen.

In often included embodiments, the cell customization provided herein includes non-viral gene transfer using an electroporation device, transposition (e.g., an SB transposon), CARS that signal through endodomains (e.g., CD28/CD3-ζ, CD137/CD3-ζ, or other combinations), CARS with variable lengths of extracellular domains connecting the antigen-recognition domain to the cell surface, and/or antigen presenting cells (aAPC) derived from, for example, K562 to be able to expand CAR+ T cells. See Singh et al., Cancer Res., 68(8): 2961-2971, 2008, Singh et al., Cancer Res., 71(10): 3516-3527, 2011. The expression cassette can be comprised in a non-viral vector, such as a transposon, or a human transposon, or recombinant variant thereof.

Also, in often included embodiments are methods, reagents, and systems for stably transfecting and re-directing T cells by electroporation, or other non-viral gene transfer (such as, but not limited to sonoporation) using naked DNA. Using naked DNA, the time required to produce redirected T cells can be reduced. "Naked DNA" in this specific context means DNA encoding a chimeric T-cell receptor contained in an expression cassette or vector in proper orientation for expression.

Also contemplated herein, T cells are prepared using mRNA encoding CAR rather than or in addition to those transduced with viral CARs. See, e.g., Foster et al., Hum Gene. Ther. 2019 February; 30(2):168-178. mRNA encoding CAR permits control of toxicity to normal tissue and allows translation of CAR T-cell immunotherapies to solid tumors.

Cell customization agents also include, for example, lipofection agents. Lipofection agents are also useful with the systems and methods described herein. Lipofection agents generally comprise one or more agents to be introduced, whether protein, small molecule, nucleic acid or other agent, complexed with one or more lipids or lipid derivatives that permit or mediate interaction with target cell membrane to introduce the agent to the target cell, e.g., a target T cell.

The proteins, small molecules, polynucleotides, primary constructs, and mmRNAs described herein can be formulated using one or more liposomes, lipoplexes, or lipid nanoparticles. In some embodiments, the CAR-encoding construct can be introduced in target cells by lipd-mediated transfection. For these embodiments, the proteins, polynucleotides, primary constructs, and mmRNAs described herein can be formulated using one or more liposomes, lipoplexes, or lipid nanoparticles. Liposomes are artificially-prepared vesicles that are primarily composed of a lipid bilayer and can be used as a delivery vehicle for the administration of nutrients and pharmaceutical formulations. Liposomes can be of different sizes such as, but not limited to, a multilamellar vesicle (MLV), which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes or to activate events such as, but not limited to, endocytosis. Liposomes can contain a low or a high pH in order to improve the delivery of the pharmaceutical formulations.

In some embodiments, cell customization compositions (e.g., agents for generating CAR T cells) can include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL from Janssen Biotech, Inc. (Horsham, Pa.).

In some embodiments, cell customization compositions (e.g., agents for generating CAR T cells) can include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; all of which are incorporated herein in their entireties). As an example a liposome can contain, but is not limited to, 55% cholesterol, 20% disteroylphosphatidyl choline (DSPC), 10% PEG-S-DSG, and 15% 1,2-dioleyloxy-N,N-dimethyl-aminopropane (DODMA), as described by Jeffs et al. As another example, certain liposome formulations can contain, but are not limited to, 48% cholesterol, 20% DSPC, 2%

PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dime thylaminopropane (DLenDMA), as described by Heyes et al.

In some embodiments, the proteins, polynucleotides, small molecules, primary constructs and/or mmRNA are formulated in a lipid vesicle that have crosslinks between functionalized lipid bilayers.

In some embodiments, the proteins, polynucleotides, small molecules, primary constructs and/or mmRNA are formulated in a lipid-polycation complex. The formation of the lipid-polycation complex can be accomplished by methods known in the art and/or as described in U.S. Pub. No. 20120178702, herein incorporated by reference in its entirety. As a non-limiting example, the polycation can include a cationic peptide or a polypeptide such as, but not limited to, polylysine, polyornithine and/or polyarginine. In another embodiment, the polynucleotides, primary constructs and/or mmRNA can be formulated in a lipid-polycation complex which can further include a neutral lipid such as, but not limited to, cholesterol or dioleoyl phosphatidylethanolamine (DOPE).

The selection of the liposome formulation can be influenced by, for example, the selection of the cationic lipid component, the degree of cationic lipid saturation, the nature of the PEGylation, ratio of all components and biophysical parameters such as size. In some embodiments, the ratio of PEG in the LNP formulations can be increased or decreased and/or the carbon chain length of the PEG lipid can be modified from C14 to C18 to alter the pharmacokinetics and/or biodistribution of the LNP formulations. The cationic lipid can be selected from any lipid known in the art such as, but not limited to, DLin-MC3-DMA, DLin-DMA, C12-200 and DLin-KC2-DMA.

In some embodiments, the cationic lipid can be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893, 302 and 7,404,969 and US Patent Publication No. US20100036115; each of which is herein incorporated by reference in their entireties. In another embodiment, the cationic lipid is selected from formula A described in International Publication Nos. WO2012040184, WO2011153120, WO2011149733, WO2011090965, WO2011043913, WO2011022460, WO2012061259, WO2012054365 and WO2012044638; each of which is herein incorporated by reference in their entireties. In other embodiments, the cationic lipid is selected from, formula CLI-CLXXIX of International Publication No. WO2008103276, formula CLI-CLXXIX of U.S. Pat. No. 7,893,302, formula CLI-CLXXXXII of U.S. Pat. No. 7,404, 969 and formula I-VI of US Patent Publication No. 0520100036115; each of which is herein incorporated by reference in their entireties. As non-limiting examples, the cationic lipid is selected from (20Z,23Z)—N,N-dimethyl-nonacosa-20,23-dien-10-amine, (17Z,20Z)—N,N-dimemyl-hexacosa-17,20-dien-9-amine, (1Z, 19Z)—N5N.about.dimethylpentacosa.about.16, 19-dien-8-amine, (13Z,16Z)—N,N-dimethyldocosa-13J16-dien-5-amine, (12Z,15Z)—NJN-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z; 19Z)—N,N-dimethylpentacosa-16,19-dien-6-amine, (22Z,25Z)—N,N-dimethylhentriaconta-22,25-dien-10-amine, (21Z,24Z)—N;N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—NJN-dimethyloctacosa-19,22-dien-7-amine, N,N-dimethyl-heptacosan-10-amine, (20Z,23Z)—N-ethyl-N-methylnona-cosa-20J23-dien-10-amine, 1-[(1 1Z,14Z)-1-nonylicosa-1 1,14-dien-1-yl] pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N, N-dimethyltritriacont-24-en-10-amine, (20Z)—N,N-dim-ethylnonacos-20-en-10-amine, (22Z)—N,N-dimethylhen-triacont-22-en-10-amine, (16Z)—N,N-dimethylpentacos-16-en-8-amine, (12Z,15Z)—N,N-dimethyl-2-nonylhenico sa-12, 15-dien-1-amine, (13Z,16Z)—N,N-dimethyl-3-non-yldocosa-13, 16-dien-1-amine, N,N-dimethyl-1-[(1 S,2R)-2-octylcyclopropyl] eptadecan-8-amine, 1-[(1S,2R)-2-hex-ylcyclopropyl]-N,N-dimethylnonadecan-10-amine, N,N-dimethyl-1-[(1S,2R)-2-octylcyclopropyl]nonadecan-10-amine, N,N-dimethyl-21.about.[(1S,2R)-2-octylcyclo-propyl]henicosan-10-amine, N,N-dimethyl-1-1S,2S)-2-{[(1R,2R)-2-pentylcyclopropyl]methyl} cyclopropyl]nona-decan-10-amine,N,N-dimethyl-1-[(1S,2R)-2-octylcyclopro-pyl]hexadecan-8-amine, N,N-dimethyH-[(1R,2S)-2-unde-cylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropy 1]-N,N-dimethyloctadecan-9-amine, 1-[(1S,2R)-2-decylcyclopropyl]-N,N-dimethyl-pentadecan-6-amine, N,N-dimethyl-1-[(1S,2R)-2-octylcy-clopropyl]pentadecan-8-amine, R—N,N-dimethyl-1-[(9Z, 12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octy-loxy)propan-2-amine, 1-{2-[(9Z,12Z)-octadeca-9,12-dien-1-yloxy]-1-[(octyloxy) methyl] ethyl}pyrrolidine, (2S)—N,N-dimethyl-1-[(9Z,12Z)-octadeca-9,12-dien-1-yloxy]-3-[(5Z)-oct-5-en-1-yloxy] propan-2-amine, 1-{2-[(9Z,12Z)-octadeca-9,12-dien-1-yloxy]-1-[(octyloxy) methyl]ethyl}azetidine, (2S)-1-(hexyloxy)-N,N-dimethyl-3-[(9Z,12Z)-octadeca-9,12-dien-1-yloxy]pro-pan-2-amine, (2S)-1-(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-am-me (Compound 9); (2S)—N,N-dimethyl-1-[(6Z,9Z,12Z)-octadeca-6,9,12-trien-1-yloxy]-3-(octyl-oxy) propan-2-amine, (2S)-1-[(11Z,14Z)-icosa-11,14-dien-1-yloxy]-N,N-dimethyl-3-(pentyloxy)pro-pan-2-amine, (2S)-1-(hexyloxy)-3-[(11Z,14Z)-icosa-11,14-dien-1-yloxy]-N,N-dimethylprop-an-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)-docosa-13, 16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-di-en-1-yloxy]propan-2-amine, N,N-dimethyl-1-(octyloxy)-3-({8-[(1S,2S)-2-{[(1R,2R)-2-pentylcyclopropyl]-methyl}cyclopropyl]oxy)propan-2-amine, N,N-dimethyl-1-{[8-(2-oclylcyclopropyl)octyl]oxy}-3-(octyloxy)propan-2-am-me and (11E,20Z,23Z)—N;N-dimethylnonacosa-11,20,2-trien-10-amine or a pharmaceutically acceptable salt or stereoisomer thereof.

In some embodiments, the LNP formulations of the polynucleotides, primary constructs and/or mmRNA (e.g., for use as agents for generating CAR T cells) can contain PEG-c-DOMG between and including 1.5-3% lipid molar ratio. In some embodiments, the pharmaceutical compositions of the polynucleotides, primary constructs and/or mmRNA include at least one of the PEGylated lipids described in International Publication No. 2012099755, herein incorporated by reference. In some embodiments, the LNP formulation contains PEG-DMG 2000 (1,2-dimyristoyl-sn-glycero-3-phophoethanolamine-N4methoxy(polyethylene glycol)-2000), a cationic lipid known in the art, and at least one other component. As a non-limiting example, the LNP formulation can contain PEG-DMG 2000, DLin-DMA, DSPC and cholesterol.

In some embodiments, the LNP formulation can be formulated by the methods described in International Publication Nos. WO2011127255 or WO2008103276, each of which is herein incorporated by reference in their entireties. As a non-limiting example, modified RNA can be encapsulated in LNP formulations as described in WO2011127255 and/or WO2008103276; each of which is herein incorporated by reference in their entireties.

In some embodiments, the LNP formulations comprise a polycationic composition. In some embodiments, the LNP formulations additionally comprise a permeability enhancer molecule. Non-limiting permeability enhancer molecules are described in US Patent Publication No. US20050222064; herein incorporated by reference in its entirety.

Lipid nanoparticle formulations (e.g., for use with agents for generating CAR T cells) for use with the systems and methods described herein can be improved by replacing the cationic lipid with a biodegradable cationic lipid, which is known as a rapidly eliminated lipid nanoparticle (reLNP). The rapid metabolism of the rapidly eliminated lipids can improve the tolerability and therapeutic index of the lipid nanoparticles. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain. The internal ester linkage can be located on either side of the saturated carbon.

In some embodiments, a protein, small molecule, polynucleotide, primary construct, or mmRNA is formulated as a lipoplex, such as, without limitation, the ATUPLEX system, the DACC system, the DBTC system and other siRNA-lipoplex technology from Silence Therapeutics (London, United Kingdom), STEMFECT from STEMGENT (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in their entireties).

In some embodiments, the protein, small molecule, polynucleotide, primary construct, or mmRNA is formulated as a solid lipid nanoparticle. A solid lipid nanoparticle (SLN) can be spherical with an average diameter between 10 to 1000 nm. SLN possess a solid lipid core matrix that can solubilize lipophilic molecules and can be stabilized with surfactants and/or emulsifiers. The lipid nanoparticle can be a self-assembly lipid-polymer nanoparticle (see Zhang et al., ACS Nano, 2008, 2 (8), pp 1696-1702; herein incorporated by reference in its entirety).

Liposomes, lipoplexes, or lipid nanoparticles can be used to improve the efficacy of polynucleotide, primary construct, or mmRNA directed protein production as these formulations can increase cell transfection by the polynucleotide, primary construct, or mmRNA; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles can also be used to increase the stability of the polynucleotide, primary construct, or mmRNA used with the systems and methods described herein.

The proteins, polynucleotides, small molecules, primary constructs, or the mmRNA agents for generating CAR T cells used with the systems and methods described herein can, in some embodiments, be encapsulated into a lipid nanoparticle or a rapidly eliminating lipid nanoparticle, and the lipid nanoparticles or a rapidly eliminating lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE (Nanotherapeutics, Inc. Alachua, Fla.), HYLENEX (Halozyme Therapeutics, San Diego Calif.), surgical sealants such as fibrinogen polymers (Ethicon Inc. Cornelia, Ga.), TISSELL (Baxter International, Inc Deerfield, Ill.), PEG-based sealants, and COSEAL. (Baxter International, Inc Deerfield, Ill.).

The proteins, polynucleotides, small molecules, primary constructs, and/or the mmRNA agents for generating CAR T cells can be encapsulated in a therapeutic nanoparticle. Therapeutic nanoparticles can be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, and U.S. Pat. No. 8,206,747; the contents of each of which are herein incorporated by reference in their entireties.

The nanoparticles used with proteins, small molecules, polynucleotides, primary constructs, or the mmRNA in (e.g., the agents for generating CAR T cells for use with) the systems and methods described herein can comprise a polymeric matrix. As a non-limiting example, the nanoparticle can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

The nanoparticles used with proteins, small molecules, polynucleotides, primary constructs, or the mmRNA in (e.g., the agents for generating CAR T cells for use with) the systems and methods described herein can comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

The nanoparticles used with proteins, small molecules, polynucleotides, primary constructs, or the mmRNA in the agents for generating CAR T cells for use with the systems and methods described herein can comprise at least one cationic polymer described herein and/or known in the art.

The cell customization agents such as nanoparticles used with proteins, small molecules, polynucleotides, primary constructs, or the mmRNA in (e.g., the agents for generating CAR T cells for use with) the systems and methods described herein can comprise at least one amine-containing polymer such as, but not limited to polylysine, polyethylene imine, poly(amidoamine) dendrimers and combinations thereof.

The nanoparticles used with proteins, small molecules, polynucleotides, primary constructs, or the mmRNA in (e.g., the agents for generating CAR T cells for use with) the systems and methods described herein can comprise at least one degradable polyester that can contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

The proteins, polynucleotides, small molecules, primary constructs, or mmRNA (e.g., for generating CAR T cells) for use with the systems and methods described herein can be encapsulated in, linked to and/or associated with synthetic nanocarriers. The synthetic nanocarriers can be formulated using methods known in the art and/or described herein. As a non-limiting example, the synthetic nanocarriers can be formulated by the methods described in International Pub Nos. WO2010005740, WO2010030763 and US Pub. Nos. US20110262491, US20100104645 and US20100087337, each of which is herein incorporated by reference in their entireties. In some embodiments, the synthetic nanocarriers can contain reactive groups to release the polynucleotides, primary constructs and/or mmRNA described herein (see International Pub. No. WO20120952552 and US Pub No. US20120171229, each of which is herein incorporated by reference in their entireties).

The proteins, polynucleotides, small molecules, primary constructs, or the mmRNA (e.g., for generating CAR T cells) for use with the systems and methods described herein can be conjugated with another compound. Non-limiting examples of conjugates are described in U.S. Pat. Nos. 7,964,578 and 7,833,992, each of which are herein incorporated by reference in their entireties. In another embodiment, the polynucleotides, primary constructs and/or can be conjugated with conjugates of formula 1-122 as described in U.S. Pat. Nos. 7,964,578 and 7,833,992, each of which are herein incorporated by reference in their entireties. As described in U.S. Pub. No. 20100004313, herein incorporated by reference in its entirety, a gene delivery composition can include a nucleotide sequence and a poloxamer. For example, the polynucleotide, primary construct and/or mmRNA can be used in a gene delivery composition with the poloxamer described in U.S. Pub. No. 20100004313.

The proteins, polynucleotides, small molecules, primary constructs, and mmRNAs (e.g., for generating CAR T cells) for use with the systems and methods described herein can be formulated with peptides and/or proteins in order to increase introduction of the proteins, polynucleotide, primary construct, or mmRNA to the cells. Such formulations can be used to increase cell transfection by the polynucleotide, primary construct, or mmRNA, alter the biodistribution of the polynucleotide, primary construct, or mmRNA (e.g., by targeting specific tissues or cell types), and/or increase the translation of encoded protein. Such peptides include, but are not limited to, cell penetrating peptides and proteins and peptides that enable intracellular delivery. A non-limiting example of a cell penetrating peptide that can be used with pharmaceutical formulations includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28): 3597-611 (2003); and Deshayes et al., Cell. Mol. Life Sci. 62(16):1839-49 (2005), all of which are incorporated herein by reference in their entireties). The compositions can also be formulated to include a cell penetrating agent, e.g., liposomes, which enhance delivery of the compositions to the intracellular space. Polynucleotides, primary constructs, and mmRNA can be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106: 6111-6116; Sawyer, Chem Biol Drug Des. 2009 73:3-6; Verdine and Hilinski, Methods Enzymol. 2012; 503:3-33; all of which are herein incorporated by reference in their entireties. The proteins, polynucleotides, small molecules, primary constructs, or mmRNAs (e.g., for generating CAR T cells) for use with the systems and methods described herein can be encapsulated within and/or adsorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides, primary constructs, or mmRNAs for generating CAR T cells for use with the systems and methods described herein can be encapsulated in a non-viron particle, which can mimic the delivery function of a virus (see International Pub. No. WO2012006376, herein incorporated by reference in its entirety).

The proteins, polynucleotides, small molecules, primary constructs, or mmRNAs (e.g., for generating CAR T cells) for use with the systems and methods described herein can be attached or otherwise bound to at least one nanotube such as, but not limited to, rosette nanotubes, rosette nanotubes having twin bases with a linker, carbon nanotubes and/or single-walled carbon nanotubes. The polynucleotides, primary constructs or mmRNAs can be bound to the nanotubes through forces such as, but not limited to, steric, ionic, covalent and/or other forces. In some embodiments, the nanotube can release one or more polynucleotides, primary constructs, or mmRNAs into cells. The size (dimensions) and/or the surface structure (e.g., functional groups attached to the building block of the nanotube) can be altered so as to alter the properties, govern the interaction of the nanotubes within the body, and/or to attach or bind to the polynucleotides, primary constructs, or mmRNA used with the systems and methods described herein can. The nanotube can also be coated with delivery enhancing compounds including polymers, such as, but not limited to, polyethylene glycol. Rosette nanotubes can also be used in some embodiments, such as those described in PCT Publication No. WO2012094304, herein incorporated by reference in its entirety.

Lymphodepletion involves the destruction of lymphocytes and T cells, typically by total body irradiation (TBI) or chemotherapeutic agents (e.g., fludarabine, cyclophosphamide, etc.), prior to immunotherapy. Although high-dose irradiation together with hematopoietic stem cell (HSC) transplantation has been shown to increase treatment efficacy in, for example, adoptive cell transfer, the relationship between the intensity of lymphodepletion and tumor treatment efficacy has not been evaluated. Nevertheless, it is known that along with increasing levels of TBI comes elevated levels of systemic inflammatory cytokines. See, e.g., Wrzesinski et al., J Immunother. 2010 January; 33(1): 1-7. It is known that high-intensity TBI can be associated with multiple toxicities, including prolonged neutropenia and an associated risk of infection, mucositis, graft failure, engraftment syndrome, diffuse alveolar hemorrhage, interstitial pneumonitis, bronchiolitis obliterans, secondary myelodysplastic syndrome, secondary malignancy, cataracts, renal insufficiency, among other effects. Pulmonary-related TBI complications, for example, have been known to be significant and a major cause of mortality. See, e.g., Muranski et al., Nat Clin Pract Oncol. 2006 December; 3(12): 668-681. Though not intending to be bound by theory, the presently described, techniques, methods, and systems can avoid the risks of lymphodepletion therapy since bedside cell therapy via cost and ease to patient enables the more routine use of the therapy (frequency) which allows multiple treatments over time which is more efficacious than a single treatment used in most current autologous cell therapies. The primary reasons for the radio/chemotherapy preparative regimen is to make space so that there is homeostatic proliferation of the therapeutic cells and/or to create a more favorable environment for therapeutic cell activity. Since this device enables routine multiple therapies or increased frequency this ensures sustained therapeutic cells over time in a different mechanism that does not require or decreases the need for chemotherapy lymphodepletion thus significantly reducing morbidity, safety risk and cost associated with this preconditioning. In the case of oncology there has been suggested that chemotherapy alters the tumor microenvironment enabling better tumor killing by CAR-T, as an example Neelapu, *Blood* 2019 133:1799-1800. Again, frequent treatments and addition of other co-therapies such as cytokines, Treg reducing agents, checkpoint inhibitors, etc. will all lead to ways to obviate this chemotherapy used in conjunction with the herein described bedside approach.

In certain embodiments, the presently described, techniques, methods, and systems are utilized to provide gene therapy for sickle cell anemia, or hemophilia and/or beta-thalassemia. For example, in the therapy for sickle cell anemia, hematopoietic stem cells are modified to introduce the normal or a therapeutic beta globin gene, which is defective in people with sickle cell disease. In hemophilia therapy regimen, cells are modified to introduce a therapeutic factor VIII or clotting factor IX gene. In the therapy for beta-thalassemia, hematopoietic stem cells are modified to introduce a the normal β-globin or γ-globin gene into hematopoietic stem cells.

Cell Customization Module

Another component of the modular bedside systems described herein is the "cell customization module" (CCM). During use of the systems described herein, the cell customization module (400) receives fluid comprising nucleated blood cells or enriched target cells from the cell separation module (200) or from a cell washing module (210, 310 or 410), if present (as shown in the exemplary embodiment in FIG. 1). The cell customization module (400) is designed and configured to receive the nucleated blood cell fraction, sometimes enriched for a target cell type or population, and then deliver one or more customizing or modifying agents to the target nucleated blood cells or an enriched fraction thereof, thereby generating customized and modified cells. As noted herein the systems may be utilized in conjunction with the modification/editing of a variety of cell types including for chimeric antigen receptor cells, backpack cells, antigen presenting cells (e.g., dendritic cells, macrophages, B cells), B cells, natural killer cells, natural killer T cells, hematopoetic stem cells (e.g., for Beta thalassemia, sickle cell, etc.), and other lymphoid cells.

The systems and methods described herein comprise a cell customization module (400) that permits the introduction of an agent to nucleated blood cells or a targeted fraction thereof separated by the cell separation module (200). The cell customization module can comprise an apparatus for introducing an agent to a cell via any of a number of techniques, including, but not limited to, electroporation, microfluidic (also referred to herein as "squeeze") transfection, lipofection, nucleofection, microinjection, biolistics, liposomes, immunoliposomes, polycation, lipid:nucleic acid conjugates, or any combination thereof, connected to the system described herein so as to permit bedside, patient-connected, continuous- or closed-loop cell customization, as described herein.

For certain ones of the various embodiments of the cell customization module and the entire system, it is specifically contemplated that one or more modules can comprise one or more sets of consumable items designed for single use with the system. Such a design not only avoids issues with potential cross-contamination of materials from different patients, but also permits flexibility with regard to the modifying agent, such that cassettes with different agents can be prepared, e.g., in kit form, to address a variety of different indications that will benefit from different agents being introduced.

For any of the cell-customization modules described herein, the cell customization agent, e.g., nucleic acid, protein or other molecule to be introduced to and modify the target cell population can be added to the system, e.g., via a port in the tubing or other conduit between the cell separation (200) or cell washing module (210, 310 or 410) and the cell customization module (400), via a port in or conduit connected to the cell customization module or chamber, or can be, for example, placed in the customization module or a chamber therein before use or via the drug/genetic material administration port (405). The placement of the agent in the customization module, e.g., as a dried reagent or as a solution or suspension prior to use is well-suited for embodiments in which the customization module is designed to include a single-use cassette. Non-limiting examples include an electroporation cuvette with DNA deposited therein prior to use, a flow-through electroporation cassette with DNA deposited in dry form therein, and a flow-through electroporation cassette or microfluidic transfection chip with a reservoir of DNA solution in fluid communication, e.g., via a Venturi port or a valve, with a fluidic electroporation or microfluidic transfection channel.

The cell customization module, in some embodiments, is designed to allow for one or more of various steps for incubating the enriched for cells and cell populations, such as enriched for CD4+ T cell populations, or subpopulation(s) thereof, or enriched for CD8+ T cell populations. In some embodiments, the target cell populations are incubated in a culture-initiating composition inside the cell customization module and/or in a holding unit that allows for optimal culture conditions to occur, for example. These incubation steps can include culture, cultivation, stimulation, activation, propagation, including by incubation in the presence of stimulating conditions, for example, conditions designed to induce proliferation, expansion, activation, and/or survival of cells in the population, to mimic antigen exposure, and/or to prime the cells for genetic engineering, such as for the introduction of a genetically engineered antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. Thus, in various embodiments, the cell customization module, or a holding unit or chamber connected to it, can include means for temperature control and/or controlled oxygen/$CO_2$ concentrations, as well as ports for the introduction of medium and other reagents for establishing or maintaining conditions to promote a desired cellular state or customization outcome.

Slipstream is another technique or platform/module useable in the presently contemplated systems. In such a technique or platform deep-primed T Cells are produced using an apheresis-based technique such as those described in, e.g., WO2019010222, WO2019010219, WO2019010224, each of which are incorporated herein by reference in their entireties. In a related exemplary embodiment, T Cells and monocytes are isolated. Monocytes are then matured into dendritic cells and used to prime the T cells with multiple tumor-associated antigens. A blend of CD4 and CD8 cells is produced. The T cells then are expanded to produce several billion tumor-targeting-primed, high-viability CD4+ and CD8+ T cells. An agent such as an immune-stimulatory drug, is then tethered to the surface of the antigen-primed T cells, which are then returned to the patient.

Cell Customization Module for Generating CAR T Cells

As exemplary of how the system may be utilized in conjunction with the modification/editing of other cell types including chimeric antigen receptor cells, backpack cells, antigen presenting cells (e.g., dendritic cells, macrophages, B cells), B cells, natural killer cells, natural killer T cells, hematopoetic stem cells (e.g., for Beta thalassemia, sickle cell, etc.), and other lymphoid cells, the systems and methods described herein provide novel and efficient ways for generating patient-specific, customized immunotherapies, for example CAR T cells, in a bedside connected manner. By eliminating the need for ex vivo expansion steps, in part, by using the patient's own body as an incubator, the systems and methods allow for the generation of CAR T cells not only in a more efficient manner, but in a way that minimizes contamination, as well as minimizes the issue of cytokine-associated toxicity, also referred to as a "cytokine storm" or cytokine release syndrome (CRS). As known to those of skill in the art, CRS is a common and potentially lethal complication of CAR-T cell therapy. CRS is a non-antigen specific toxicity that can occur as a result of the high-levels of CAR-T cell expansion and immune activation typically required to mediate clinical benefit using immunotherapies such as CAR-T cell transfer. Timing of symptom onset and CRS severity depends on the inducing agent and the magnitude of immune cell activation. Symptom onset typically occurs days to occasionally weeks after T cell infusion, coinciding with maximal in vivo T-cell expansion.

The systems described herein avoid the ex vivo expansions steps typically associated with CAR T therapies by utilizing a cell customization module (CCM) where separated and, optionally, selected blood cells, are directly contacted with therapeutic agents for generating CAR T cells. The cell customization module (400) receives fluid comprising nucleated blood cells or enriched target cells from the cell separation module (200) or from a cell washing module (210 or 310), if present (as shown in the exemplary embodiment in FIG. 1). The cell customization module (400) is designed and configured to receive the nucleated blood cell fraction, sometimes enriched for a target cell type or population, and then deliver one or more agents for generating CAR T cells to the target nucleated blood cells or an enriched fraction thereof, thereby generating customized CAR T cells.

The cell customization module can comprise an apparatus for introducing an agent to a cell via any of a number of techniques, including, but not limited to, electroporation, transfection such as microfluidic (also referred to herein as "squeeze") transfection, lipofection, nucleofection, microinjection, sonoporation, magnetic nanoparticle, biolistics, liposomes, immunoliposomes, polycation, lipid:nucleic acid conjugates, or any combination thereof, connected to the system described herein so as to permit bedside, patient-connected, continuous- or closed-loop generation of CAR T cells, as described herein.

For certain ones of the various embodiments of the cell customization module, it is specifically contemplated that one or more modules can comprise one or more cassettes designed for single use. Such a design not only avoids issues with potential cross-contamination of materials from different patients, but also permits flexibility with regard to the agents for generating CAR T cells, such that cassettes with different agents can be prepared, e.g., in kit form, to target a variety of different antigens that will benefit from different agents for generating CAR T cells being introduced.

The agents for generating CAR T cells can be added to the system, e.g., via a port in the tubing or other conduit between the cell separation (200) or cell washing module (210, 310 or 410) and the cell customization module (400), via a port in or conduit connected to the cell customization module or chamber, or can be, for example, placed in the customization module or a chamber therein before use or via the drug/genetic material administration port (405). The placement of the agents for generating CAR T cells in the cell customization module, e.g., as a dried reagent or as a solution or suspension prior to use is well-suited for embodiments in which the customization module is designed to include a single-use cassette. Non-limiting examples include an electroporation cuvette with DNA deposited therein prior to use, a flow-through electroporation cassette with DNA deposited in dry form therein, and a flow-through electroporation cassette or microfluidic transfection chip with a reservoir of DNA solution in fluid communication, e.g., via a Venturi port or a valve, with a fluidic electroporation or microfluidic transfection channel.

The cell customization module, in some embodiments, is designed to allow for one or more of various steps for incubating the enriched for cells and cell populations, such as enriched for CD4+ T cell populations, or subpopulation(s) thereof, or enriched for CD8+ T cell populations. In some embodiments, the target cell populations are incubated in a culture-initiating composition inside the cell customization module and/or in a holding unit that allows for optimal culture conditions to occur, for example. These incubation steps can include culture, cultivation, stimulation, activation, propagation, including by incubation in the presence of stimulating conditions, for example, conditions designed to induce proliferation, expansion, activation, and/or survival of target T cells in the population, to mimic antigen exposure, and/or to prime the cells for genetic engineering, such as for the introduction of a genetically engineered chimeric antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. Thus, in various embodiments, the cell customization module, or a holding unit or chamber connected to it, can include means for temperature control and/or controlled oxygen/$CO_2$ concentrations, as well as ports for the introduction of medium and other reagents for establishing or maintaining conditions to promote a desired cellular state or customization outcome.

In some embodiments of the systems and methods described herein, the customized CAR T cells are activated and/or accumulated within the system to reach therapeutically sufficient numbers prior to administration to a subject. For example, the cells can be activated to proliferate either non-specifically with mitogenic anti-CD3 and anti-CD28 antibodies, or through the use of genetically modified antigen-presenting cell lines or particles which display the antigen targeted by the CAR binding domain (and in some cases additional costimulatory molecules). Other methods to selectively propagate T cells to constitutively express CAR include co-expression with transgenes for selection under cytocidal concentrations of drug. Antigen-specific activation is preferred, as CAR-mediated T-cell activation is thought to depend on and to increase with the binding affinity to cognate antigen. In the event that the CAR-T cells are non-specifically activated prior to customization with a nucleic acid agent for generating CAR T cells, they can be specifically activated within the system prior to reintroduction to a subject, again using cell lines or particles that display the antigen targeted by the CAR binding domain. Such activation steps can occur, in some embodiments, in a holding chamber as described herein.

The following describes various embodiments of cell customization modules suited for use in the methods and systems described herein.

Electroporation Module Embodiments

In some embodiments, the cell customization module comprises an electroporation module (420). Electroporation applies an electric field to cells to introduce pores, termed electropores, to the cell membrane through which (usually charged) macromolecules or agents can flow into the cell. Removal of the field permits the pores to re-seal, with the introduced molecules inside the cell. In certain embodiments, the electroporation module comprises a flow electroporation chamber. For example, a chamber or system described in U.S. Pat. Nos. 5,720,921, 6,074,605 and/or 7,141,425, each of which is incorporated herein by reference in its entirety. Alternative non-limiting exemplary systems for electroporation are contemplated, for example, those detailed in U.S. Pat. Nos. 7,521,224, 8,673,623, and U.S. Patent App. Pub. Nos. 20070128708A1, 20080182251A1, US20130196441, 20170233716A1, and Kim et al., Biosens Bioelectron 2008 23(9):1353-60, each of which is incorporated herein by reference in its entirety.

Electroporation occurs when the transmembrane potential exceeds a critical threshold value (generally about 0.25-1 V). The transmembrane potential ($\Delta\psi E$) is determined by $\Delta\psi E = 0.75\ g(\lambda)aE\ \cos\theta$, where $g(\lambda)$ is a function of the membrane and buffer conductivities, a is the diameter of the cell, E is the field strength and $\theta$ is the angle between the normal to the membrane surface and the field direction (Weaver & Chizmadzhev, Bioelectrochem. Bioener. 41:135-160 (1996)). A pulsed field of alternating strengths is often used to beneficial effect—it has been proposed that a first pulse of a stronger field strength generates an electropore, and a subsequent pulse at lower strength pushes the desired molecules, e.g., nucleic acid, through the pore through electrophoresis.

Electroporation has been used for decades to introduce nucleic acids and other molecules to prokaryotic and eukaryotic cells. One of the advantages of electroporation is that it is not particularly cell-type dependent—while exact conditions may vary for optimal delivery, most cell types can be successfully electroporated to deliver, e.g., nucleic acids, proteins or other agents to the cell.

Methods and devices for electroporation of mammalian cells are known in the art and can be adapted for use in the methods and systems described herein. Electroporation methods and devices are described, for example, in U.S. Pat. Nos. 4,695,547; 4,764,473; 4,882,281; 4,946,793; 4,906,576; 4,923,814; and 4,849,089, each of which are incorporated herein by reference in their entireties.

Important parameters for successful electroporation include the maximum voltage applied and the duration of the current pulse. The voltage and capacitance settings should also be optimized for each cell type, with the resistance of the electroporation buffer being important for choosing the initial instrument settings. Optimal stable and transient transformation occur at about the same instrument settings, so transient expression can be used to optimize conditions when adapting to a new cell type.

For low-resistance (high-salt) buffers such as PBS, HeBS, or tissue culture medium, one can start with a capacitor setting of 25 µF and a voltage of 1200 V for an arrangement in which electrodes are 0.4 cm apart, then increase or decrease the voltage until optimal transfection is obtained. For many cell types, the choice between PBS, HeBS, and tissue culture medium makes little difference. However, primary cells, such as nucleated blood cells removed from a patient, tend to be easily killed and thus electroporate poorly at the high voltages needed for PBS or HeBS electroporation buffers. For these cells, tissue culture medium can be better for electroporation, although it has been noted that calcium and magnesium ions in such medium lower the electroporation efficiency. Phosphate-buffered sucrose can be optimized at voltages several hundred volts below those used with PBS or HeBS. Alternatively, many sensitive cells electroporated more effectively in HeBS with a low voltage/high capacitance setting that provided an at least 10-fold longer pulse duration. For example, one can start at 250

V/960 μF and increase the voltage up to 350 V or decrease down to 100 V in steps to determine optimal settings.

The application of high-voltage electrical pulses rapidly generates heat, which can kill the cells; keeping cells cold (e.g., at 0° C.) often improves cell viability and thus results in higher effective transfection frequency—in one embodiment, the system described herein includes a means for cooling a cell preparation or for maintaining a low temperature to counter heating that occurs during electroporation. That said, some have found that better electroporation efficiencies are achieved at room temperature, so cooling is not always critical.

Another factor contributing to loss of viability appears to be the pH change that results from electrolysis at the electrodes. The impact of this can be reduced, for example by replacing some of the ionic strength of the PBS with extra buffer (e.g., 20 mM HEPES, pH 7.5).

Electroporation has most often been performed in batch form, in relatively small volumes (around 1 ml, and often about $1\times10^6$ cells) by placing a suspension of cells and macromolecules to be introduced into a cuvette including two electrodes which are connected to a pulse generator and arranged to deliver current through the suspension. In the batch format, one or more electric field pulses are applied to the cells, and treated cells are generally transferred to medium to permit the cells to recover. In one embodiment, a batch processing mode can be used in the methods and systems described herein, e.g., by shunting a suspension of collected target cells into an electroporation chamber when a given concentration of target cells is reached (and detected by a detector) in the cell separation module (200), adding a cell-modifying or cell-customizing agent such as an agent for generating CAR T cells (e.g., DNA, RNA, or a protein) to the chamber, and applying one or more electric pulses from a pulse generator to the cell suspension. In one embodiment, the cells are washed before the electroporation step, e.g., to remove plasma proteins and/or to put the cells into a solution with ionic properties better-suited than plasma for electroporation—generally, electroporation is performed in solutions of relatively low ionic strength. Buffers and solutions suited for electroporation are known in the art, and described herein below. A cell washing unit is described herein above.

Batch electroporated cells can be re-introduced into the patient as each batch of cells is electroporated, or continuously if continuous electroporation is utilized. Alternatively, the electroporated cells can be delivered to a holding, incubating or collection unit (440), whether a chamber in the system described herein, a bag or other unit permitting the cells from a plurality of electroporation processes to be collected, optionally incubated and/or sampled to evaluate, e.g., electroporation efficiency, cell viability or other parameter, before the cells are re-introduced to the patient. The holding, incubating or collection unit (440) can be connected to or part of a sampling unit (450B) for in-line testing and analysis or external sampling for testing and analysis of the final cellular product prior to delivery to patient, and/or a detector (500) as described herein, to facilitate or permit the evaluation of desired parameters for the electroporated cells. It is noted here that any of the cell customization modules incorporated in a system as described herein (e.g., for electroporation, microfluidic transfection, lipofection, etc.) can incorporate a holding, incubating or collection unit (440) as described here. Similarly, any of the cell customization modules described herein can alternatively, or in addition, direct cells to a purification module (460) that permits, for example, removal of excess customization reagent and/or removal of damaged or non-viable cells.

While batch electroporation can be used in the methods and systems described herein, an advantage can be provided by flow-through or continuous-flow electroporation. In this process, cells, together with a cell-customization agent, such as an agent for generating CAR T cells, to be introduced, are passed through an electroporation unit through which a voltage is constantly applied. Systems for continuous flow electroporation are described, for example, by Wei & Li, Methods Mol. Biol. 1121: 99-110 (2014) (titled "Continuous cell electroporation for efficient DNA and siRNA delivery based on laminar microfluidic chips") and Geng et al., J. Controlled Release 144: 91-100 (2010) (titled "Flow-through electroporation based on constant voltage for large volume transfection of cells"), both of which are incorporated herein by reference. Geng et al. not only describe an effective design for flow-through electroporation of mammalian cells (CHO cells), but they describe in detail the scale-up of a prototype to achieve treatment of up to 20 ml of cell suspension per minute, with efficiency as high as 75%. U.S. Pat. No. 10,253,316, incorporated herein by reference, suggests treatment of up to 1 to $10^{10}$ cells per second, $10^4$ to $10^7$ per second, $10^5$ to $10^8$ per second, or $10^6$ to $10^9$ per second, or batches of cells ranging from 1 cell to $10^{10}$ cells in a single transformation procedure with efficiency rates ranging up to 95% or greater. The devices described by Geng et al. incorporate a fluidic channel that has constant depth, but varies in width over its length, such that some portions are narrow and others are wider. The electric field at any point is determined by the width of the channel, with narrower portions having a stronger field than wider ones. Widths and current are selected such that the field only exceeds the transmembrane potential permitting electroporation at the narrow points, and alternating narrow and wider sections over the length of the channel provides an effect that approximates that of a pulsed field, without the need for a pulsed field generator. The flow rate through the channel, as well as the respective lengths of the wide and narrow sections, can be adjusted to adjust the time during which cells are exposed to current strong enough to electroporate them. This design is well-suited for a flow-through electroporation module (420) for use in the methods and systems described herein. Other flow-through electroporation devices are described, for example, in U.S. Pat. Nos. 6,617,154, 6,673,669, 7,029,916, 7,771,984, 9,546,350, each of which is incorporated herein by reference in its entirety.

In some embodiments, a flow-through electroporation system or module employs a fluidic system fabricated from polydimethylsiloxane (PDMS) on a glass substrate, incorporating channels of with alternating wide (10,000-5,000 μm, e.g., about 7,500 μm) and narrow (500-700 μm, e.g., about 500 μm) stretches. The inlet to the module is connected to a conduit or tubing through which target cells are delivered from the cell separation module (or from a cell washing unit connected directly or indirectly to the cell separation module (200) such that cells delivered to the electroporation module (420) are suspended in electroporation buffer) to the electroporation module. Wire electrodes inserted into the inlet and outlet of the flow-through module are connected to a constant voltage power supply. Cells in suspension in electroporation buffer and including cell-customizing agents (e.g., agents for generating CAR T cells), including, but not limited to DNA or RNA, are pumped through the fluidic channel while DC voltage is applied across the channel Throughput can be increased, for example, by incorporating more than one such fluidic construct in the system, e.g., arranged in parallel.

Electroporated cells emerging from the flow-through electroporation channel can be immediately re-introduced to the patient, or, as with the batch-electroporated cells, can be delivered to a holding, incubating or collection unit (440) to be collected, optionally incubated and/or sampled to evaluate, e.g., electroporation efficiency, cell viability or other parameter, before the cells are re-introduced to the patient. The holding, incubating or collection unit (440) can be connected to or part of a sampling unit (450B) and/or a detector (500) as described herein, to facilitate or permit the evaluation of desired parameters for the electroporated cells. Alternatively, or in addition, cells emerging from the electroporation module (420) can be transferred to a cell purification module (460) to permit, for example, removal of excess cell customization agents (e.g., agents for generating CAR T cells), or damaged or non-viable cells.

Cell Squeeze Microfluidic Module

In some embodiments, cell customization agents (e.g., agents for generating CAR T cells) can be introduced to target cells from the cell separation module (200) or cell wash unit (210, 310 or 410) by forcing the cells under pressure through a constriction smaller in diameter than the cell in the presence of a modifying agent (e.g., agent for generating CAR T cells). The rapid stretching, rapid compression, or pulse of high shear rate leads to uptake of molecules into the cytoplasm of the cell from the surrounding cell medium. This so-called "cell squeeze" microfluidic technology is applicable to a wide number of cell types, and well-suited for introducing materials to nucleated blood cells.

The cell squeeze microfluidic technology is described, for example, in WO2013059343 and US2014287509, which are incorporated herein by reference in their entireties. In the design described therein, the delivery of molecules into the cell is proportional, e.g., linearly or monotonically with cell velocity through a constriction and/or pressure. For example, 50 µl of cell suspension goes through the device in a few seconds. The throughput ranges between 1 cell/second per channel (or even less) to over 1,000 cells/second per channel. Typical cell velocities through the constriction include 10 mm/second to 500 mm/second, although cell velocities can be up to 10 m/s (or even higher). Additional channels can be placed in parallel to increase the overall throughput of the system. Using the design in the '343 or '509 documents, the uptake of customization agent is diffusion-based rather than endocytosis-mediated, i.e., the agent is in the cytoplasm rather than in endosomes following passage through the device. Little or none of the customization agent appears in endosomes following cell treatment. For example, large molecules are taken up more slowly than smaller molecules. Controlled cell stretching and velocity of movement of the cells through the constriction leads to effective delivery of customization agent while preserving the viability and integrity of the cells. After treatment, cell viability is generally between 70-100%, e.g., typical viability is 90% after treatment.

The cell customization module (400) comprising a cell squeeze microfluidic platform (421) can include, either upstream of the module or integrated within it, a port through which cell customization agents (e.g., agents for generating CAR T cells), e.g., nucleic acid, protein, small molecule, etc., are admixed with the cells to be forced through the microfluidic platform. As discussed above, the port can be, e.g., a Venturi port, or a valve that admits customization agent from a reservoir or other source.

The cell squeeze microfluidic platform (421) includes, in addition to one or more microfluidic channels including constrictions smaller than the target cell, a means for forcing the cells through the channels under controlled conditions. Such means can include, for example, a pump, either within or connected to the cell customization module or, alternatively, upstream of the cell customization module. It is also contemplated that the pump could be placed downstream of the cell customization module so as to draw or pull the cells through the constrictions in the module, rather than pushing them. As an alternative to a pump, a diaphragm in fluid connection with the contents of the microfluidic platform can be acted upon by a controlled source of pressure, e.g., a gas or fluid, to compress the diaphragm. In this configuration, a one-way valve upstream of the cell customization module would prevent back-flow and, when pressure is applied to the diaphragm, cells in suspension are forced through the microfluidic channel.

When a cell squeeze microfluidic platform is used in the systems or methods described herein, a microfluidic module (421) comprising one or more channels with constrictions that promote the passage of cell customization agents (e.g., agents for generating CAR T cells) into cells is connected via fluid conduit, e.g., tubing, from the cell separation module (200), or from a cell washing unit connected to (310, 410) or integrated with (210) the cell separation module. Cells flow or are pumped from the cell separation module (200) or cell washing unit (210, 310 or 410) to the squeeze microfluidic platform, where the cells admixed with cell customization agents (e.g., agents for generating CAR T cells), e.g., nucleic acid, protein, etc., are forced through the microfluidic passage(s) of the platform (421), thereby rendering the cells able to take up the customization agent.

A combination of cell squeeze microfluidic cell modification and electroporation has also been described. Passing cells at high speed through microfluidic constrictions smaller than the cell diameter mechanically disrupts the cell membrane, allowing a subsequent electric field to further disrupt the nuclear envelope and drive DNA molecules into the cytoplasm and nucleus. See, e.g., Ding et al., Nature Biomed. Eng 1: 0039 (2017), titled "High-throughput nuclear delivery and rapid expression of DNA via mechanical and electrical cell-membrane disruption." This combination can also be included in the cell customization module of a system as described herein.

Treated cells emerging from the microfluidic channel can be immediately re-introduced to the patient, or can be delivered to a holding, incubating, or collection unit to be collected, optionally incubated and/or sampled to evaluate, e.g., cell modification or customization, or efficiency of introduction of the agents for generating CAR T cells, cell viability or other parameter, before the cells are re-introduced to the patient. The holding, incubating, or collection unit can be connected to or part of a sampling unit and/or a detector as described herein, to facilitate or permit the evaluation of desired parameters for the treated cells. In some embodiments, cells emerging from the cell squeeze microfluidic cell customization module can be transferred to a cell purification module (460) that permits removal of, for example, excess cell customization agents (e.g., agents for generating CAR T cells) or damaged or non-viable cells.

Lipofection Module

In some embodiments, the cell customization module is designed to introduce nucleic acids, proteins or other molecules into cells via complexes of these molecules with lipid nanoparticles or liposomes. Such lipid nanoparticles and liposomes are described in detail elsewhere herein. In such embodiments, the cell customization module (400) comprises a lipofection module (422), which mediates the process of contacting target cells delivered to the customization module by contacting them with a lipofection reagent carrying the material (e.g., agents for generating CAR T cells) to be introduced to the cells. A lipofection module (422) comprises a chamber into which cells and lipofection reagent are introduced, e.g., via conduit or tubing from the cell selection module (200), or from a cell washing unit (210, 310 or 410) or cell enrichment unit (1100) therein or between the cell selection module and the cell customization module, respectively. Lipofection reagent can be present in the lipofection module prior to the introduction of cells, or can, for example, be introduced from a reservoir or other source via a valve or port in the lipofection chamber or the conduit leading to it. The lipofection module or the tubing or conduit leading to it can also include a valve or port connected to a reservoir or source of serum-free culture medium suitable for lipofection. The same port or valve, or alternatively another port or valve, can be connected to a source of medium containing serum or serum substitute, or, alternatively to a conduit or tubing that delivers the patient's own cell-free plasma to the lipofection chamber after the cells have incubated with lipofection reagent. In some embodiments, lipofection reagent can be supplied in a cassette lipofection module or a cassette that is inserted into the lipofection module. The cassette can include the lipofection chamber, and can, for example, include ports or connections to interface with, for example, tubing or a conduit that introduces cells, tubing or a conduit that introduces serum-free medium, and/or tubing or a conduit that introduces serum-containing medium or the patient's own plasma. Additional ports in the lipofection cassette can be connected to or connectable to tubing or a conduit leading to a holding/incubating/or collection unit as described herein, or alternatively or in addition, to a sampling unit and/or a detector as described herein. A lipofection module cassette can be a single-use cassette.

To achieve lipofection, cells are generally contacted with lipofection reagent complexed with the agent one wishes to deliver to the cells in a serum-free medium and incubated for a given period of time, followed by the re-addition of serum-containing medium or plasma. Cells subjected to lipofection can be transferred to a holding/incubating/collection unit as described herein until, for example, a desired number of cells are treated, or, for example, to permit sampling or analysis, e.g., by withdrawal of a portion of the cells to a sampling or analysis unit as described herein that can detect, for example, expression of a desired polypeptide, the presence of an indicator of lipofection, a population of a CAR T cell, or another parameter useful in monitoring customized cell status. Alternatively, cells subjected to lipofection can be transferred or directed to a purification module (460) as described herein, e.g., to remove excess lipofection reagent or otherwise purify the cells before they are reintroduced to the patient.

In addition to electroporation, microfluidic squeezing and lipofection, other approaches for the introduction of a cell customization agent to a target cell can be employed with a bedside system as described herein. Non-limiting examples include calcium phosphate mediated transfer, nucleofection, sonoporation, heat shock, magnetofection, microprojectile mediated transfer (nanoparticles), and cationic polymer mediated transfer (DEAE-dextran, polyethylenimine, polyethylene glycol (PEG) and the like) among others. Thus, it is contemplated herein that target nucleated blood cells or enriched target cells thereof can transfer from a cell separation module (200), directly or via a cell washing unit (210, 310 or 410) or a cell enrichment unit (1100) to a cell customization module (400) containing a unit or component adapted and designed to perform, e.g., sonoporation, magnetofection, nanoparticle-mediated transfer or cationic polymer-mediated transfer, among others. In such instances, cell treatment is performed under conditions appropriate to the selected approach, and cells are optionally transferred to a holding/incubating/or sampling chamber as described herein for other customization modules and customization approaches, and/or to a purification module or unit as also described herein. Processed and optionally incubated and/or analyzed cells can then be returned to the patient to complete the closed-loop cell customization therapeutic process.

The technique of sonoporation, or cellular sonication, is the use of sound (e.g., ultrasonic frequencies) for modifying the permeability of the cell plasma membrane. Sonoporation methods are known to those in the art and are used to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; all herein incorporated by reference in their entirety). Sonoporation methods are known in the art and are also taught for example as it relates to bacteria in US Patent Publication 20100196983 and as it relates to other cell types in, for example, US Patent Publication 20100009424, each of which are incorporated herein by reference in their entirety.

Sampling and/or Holding Units

Depending on the nature of the cell customization being performed in the cell customization module, in some embodiments, the systems and methods described herein permit assessment and/or adjustment of the cells or composition containing the cells, for example, after treatment of cells to customize or modify them in the cell customization module.

In some embodiments, the systems and methods described herein permit assessment and/or adjustment of the cells or composition containing the cells, for example, after treatment of cells with the agents for generating CAR T cells in the cell customization module.

In another embodiment, assessment and adjustments can be performed in a sampling unit (450B) that is connected, for example, via a valve and/or outlet conduit to the cell customization module (400) or a modification chamber (420, 421, 422) (e.g., an electroporation chamber, a microfluidic device or array, or a lipofection chamber) and sampling unit (450A) that is connected, for example, via a valve and/or outlet conduit to the cell separator (1200), cell washing unit (210) or enrichment unit (1100). The sampling units (450A, 450B) can, in some embodiments, interface with one or more detector modules (500), as described elsewhere herein.

Exemplary assessments performed in the sampling unit include taking one or more measurements of a composition or chamber containing the cells, such as assessing cells for proliferation rate, degree of survival, phenotype, e.g., expression of one or more surface or intracellular markers, such as proteins or polynucleotides, and/or assessing the composition or chamber containing the cells for temperature, media component(s), oxygen or carbon dioxide content, and/or presence or absence or amount or relative amount of one or more factors, agents, components, and/or cell types, including subtypes. In some embodiments, the assessment is performed in an automated fashion, for example, using a detector module as described herein, and/or is set ahead of time to be carried out at certain time-points during incubation of the target cell populations with one or more customization agents. In some embodiments, the outcome of the assessment in the sampling unit, such as a determined interim ratio of two types of cells, indicates that one or more adjustments should be made, such as addition or removal of one or more cell types, or addition of additional customization agents. In some embodiments, the outcome of the assessment in the sampling unit indicates that the target cell population has been sufficiently customized and can reenter the continuous, flow-through of the system and/or move to the purification module (460).

Adjustments that can be made based on assessments done in the sampling unit can include adjusting any cell culture factor or parameter, such as temperature, length (time) for which incubation or a step thereof will be carried out (duration of incubation), replenishment, addition and/or removal of one or more components in the composition being incubated, e.g., media or buffer or components thereof, agents, e.g., nutrients, amino acids, antibiotics, ions, and/or stimulatory factors, such as cytokines, chemokines, antigens, binding partners, fusion proteins, recombinant soluble receptors, or cells or cell types or populations of cells. In some embodiments, the removal or addition of various components or other adjustment is carried out in an automated fashion, for example, using a device or system as described herein. In some embodiments, the system is programmed such that an adjustment is automatically initiated based on a certain readout from an interim assessment. For example, in some cases, the system described herein is programmed to carry out one or more assessments at a particular time; the system or device in such cases can be further programmed such that a particular outcome of such an assessment, such as a particular ratio of one cell type to another, initiates a particular adjustment, such as addition of one or more of the cell types, and/or output into the purification module (460).

Preferably, any adjustments made based on assessments carried out in the sampling unit do not disrupt the closed environment of the other components and modules of the systems described herein. Accordingly, the cell customization module can further comprise additional input and/or removal conduits/valves/tubing, designed to add or remove components while maintaining sterility.

A sampling unit can also perform one or more assays to evaluate, e.g., the expression of a product encoded by an introduced nucleic acid, or the degree to which a cell customization agent (e.g., agents for generating CAR T cells) has been introduced to the cells. The sampling unit can be interfaced with a detector that detects or measures, for example, fluorescence, or other parameter indicative of cell customization, as appropriate for a given customization. In such embodiments, the assay can depend upon the type of cell customization (e.g., agents for generating CAR T cells, i.e., DNA or RNA). Where, for example, the customization introduces a construct encoding a gene product, the assay can, for example, detect the gene product, e.g., via binding of a labeled antibody to the gene product, or via conversion of a substrate to a detectable moiety when the product is an enzyme.

Non-limiting examples of markers and assays that can be used to monitor a population of CAR T cells in the sampling and/or holding chamber include the presence of antigenic markers, CD2, CD28, CTLA4, CD40 ligand (gp39), CD18, CD25, CD69 (lymphocyte activation marker) and CD16/CD56, which are known to be involved in interactions associated with T-cell and NK cell activation and immune function. The effectiveness of a leukocyte population to promote destruction of a diseased cell or pathogen can be measured by various assays. A CAR T cell population generated using the systems and methods described herein is considered effective to promote destruction of a diseased cell if, in an appropriate assay, the population exhibits cytolytic activity at a level of at least about 15% above, at least about 20% above, at least about 25% above, at least about 30% above, at least about 35% above, at least about 40% above, at least about 45% above, at least about 50% above, at least about 55% above, at least about 60% above, at least about 65% above, at least about 70% above, at least about 75% above, at least about 80% above, at least about 85% above, at least about 90% above, at least about 95% above, at least about 100% above that of a negative control population.

The sampling unit can permit the introduction, for example, of a substrate or indicator reagent. The sampling unit can also permit, for example, the introduction of a lysis reagent or can comprise, for example, a sonication probe that lyses cells, e.g., when a customizing enzyme is expressed intracellularly.

As another alternative, it is contemplated that in some instances it can be helpful to co-introduce a surrogate marker that indicates that a cell has received a customization agent. For example, when the customization agent is a nucleic acid encoding a gene product, it can be beneficial to admix the sequence encoding the desired gene product with one encoding, for example, a fluorescent protein, such as GFP. Transfected cells will express the fluorescent protein, which can be detected either in the sampling unit, e.g., via a fluorescence detector unit, or, for that matter, in the cell customization module via a fluorescence detector unit.

As another alternative, it is contemplated that in some instances it can be helpful to co-introduce a surrogate marker that indicates that a cell has received the particular agent for generating CAR T cells. For example, when the agent for generating CAR T cells is a DNA encoding a CAR, it can be beneficial to admix the sequence encoding the CAR with one encoding, for example, a fluorescent protein, such as GFP. Transfected cells will express the fluorescent protein, which can be detected either in the sampling unit, e.g., via a fluorescence detector unit, or, for that matter, in the cell customization module via a fluorescence detector unit.

It is contemplated that at least a portion of a customization preparation including nucleic acid or protein to be introduced is itself fluorescently labeled—while the label may (or may not) interfere with expression from the nucleic acid, or function of an introduced protein, if only a portion of the nucleic acid or protein is labeled, it can provide a measure of the efficiency of customization agent delivery. In such embodiments, the labeled customization agent can be, for example less than or equal to about 20% of the total, less than or equal to about 10% of the total, less than or equal to about 5% of the total, less than or equal to about 2% of the total, or less than or equal to about 1% of the total.

It is also contemplated that a surrogate indicator of cell modification can include a fluorescent polypeptide, rather than a gene encoding a fluorescent polypeptide.

In some embodiments, treated cells can exit the customization module and be transferred via tubing or conduit to a holding, incubation or collection unit (440). This unit can permit, for example, cells to recover from the sometimes harsh conditions used for cell customization (e.g., when generating CAR T cells), and, for example, begin to express a product (e.g., CAR) from an introduced nucleic acid. The holding unit can also maintain the cells until a threshold number or value is reached, such as viable cell number, detection of a level of a marker, e.g., a marker (e.g., CAR) encoded by a cell customization agent or, for example, a surrogate marker of customization or modification efficiency. The holding unit can include a port or valve to admit medium, nutrients, or other reagents. The holding or incubation unit can, for example, maintain a desired temperature and oxygen and/or $CO_2$ level(s). The holding unit can be interfaced with one or more detectors to monitor, e.g., cell number, cell viability, pH, fluorescence, etc. as appropriate for a given cell customization and the needs of cells that have been subjected to it.

According to presently contemplated embodiments, the patient-connected, closed-loop continuous-flow systems may include one or more of a electroporation module (420), a microfluidic module (421), a lipofection module (422), and/or a sonoporation module (not depicted) on a single system. As such a single patient-connected, closed-loop continuous-flow system may have all of these modules or a subset thereof. Also contemplated are patient-connected, closed-loop continuous-flow systems having only a single one of such modules.

Detectors/Detector Modules

The modular bedside systems described herein further comprise one or more detectors/detector modules (500) (FIG. 1) that interface with the various other modules. Such detector modules monitor and detect various parameters to control and regulate the flow of fluid and cells through the system, and monitor the inputs and outputs of the various modules. Such detector modules can comprise sensors such as optical sensors, acoustic sensors, liquid sensors, bubble detectors (ultrasonic detector), pressure sensors, and the like.

For example, a camera, either focused on a macroscopic window of a cell separation module (200) or focused, e.g., through a microscope objective onto a portion of a sample, can be used as a component of a detector module described herein to detect a sample that is being separated into at least two components during centrifugation. The camera as part of a detector module can be used to detect different layers formed by the separated sample in the cell separation module due to centrifugal forces. In addition, the pH value of the sample components can be measured, in some embodiments. For this purpose, an indicator is used in the cell separation or other module that changes its color dependent on the pH in the solution. Alternatively, pH can be detected via a standard or miniature pH electrode component in contact with a sample or fluid in the system. Moreover, it is possible that, in some embodiments, the temperature of the sample can be measured either via thermometer or thermocouple associated with a given component of the system, or, for example, using liquid crystals that are positioned in a chamber of, e.g., the cell separation module or other module, such that their position can be detected with a microscope camera unit from the outside.

In some embodiments, a detector comprises a fluorescence detector, which comprises an incident light source of a given wavelength or wavelengths, and a detector that collects and quantifies fluorescent light emitted when incident light excites fluorescence at another wavelength. A fluorescence detector can be designed or arranged to detect fluorescence from any of a number of common fluorescent proteins or fluorescent labels, as the case may be. A luminescence detector may also be employed to identify predetermined or preselected luminescence reports.

In some embodiments of the detector modules described herein, a detector module is configured to detect hemoglobin in the plasma components of the blood. Detected hemoglobin signifies the presence of red blood cells in the plasma components of the blood. As the red blood cells are typically separated from the cellular components of the blood prior to cell customization, the presence of hemoglobin can be used to identify any issues with the cell separation module (200) and/or modify output parameters from the cell separation module. Upon detection of hemoglobin, the circuitry can issue a warning, prevent return of fluids to the patient, and/or cease operation at least one module of the systems described herein.

Flow cell optical detection, or flow cytometric, components can also be used in some embodiments of the systems and methods described herein. Flow cell optical detection typically comprises a light (optical) source for providing light of one or more wavelengths to a fluid sample in a fluid cell and an optical detection system for detecting any interaction between the light and the sample. Light scattering is a phenomenon that occurs when there is a particle, such as a cell, that changes the traveling direction of light when the light hits it. Information about the size and material of the particle can be obtained by detecting the scattered light. Particularly, information about the size of the particle (cell) can be obtained from forward scattered light. Meanwhile, information about the inside of the particle, namely granularity of the cell, can be obtained from side scattered light. When a laser beam is applied to the cell, side scattered light intensity depends on the complexity (e.g., shape, size, and density of a nucleus, and an amount of granules) in the cell. For example, a device for performing flow cytometry, which refers to a technique for counting and examining microscopic particles, such as cells and chromosomes, by suspending them in a stream of fluid and passing them through an electronic detection apparatus, can optionally be used in the systems and methods described herein. Moreover, labeled reagents targeting a characteristic of the cells, such as an expressed receptor or protein, are also useful in flow cytometric analysis. When such reagents bind a target on the cell, they can be identified when irradiated by proper excitation wavelength light source. Multiple such targets can be identified on a single cell using different fluorescent labels and/or excitation wavelength light sources. Flow cytometry allows simultaneous, multiparametric analysis of the physical and/or chemical parameters of up to thousands of particles per second, such as fluorescent parameters. Fluorescently labeled reagents targeting a cell customization expressed in a population of cells are useful in flow cytometric detection and evaluation in the presently described systems. As noted herein above, in some embodiments, systems as described herein do not include flow cytometric separation or detection units. Embodiments requiring greater throughput or greater numbers of modified cells are generally less well suited to the use of flow cytometry.

Detection systems useful with the systems and methods described herein include microfluidic-photonic integrated circuit optical interrogation devices, such as those described in U.S. Pat. No. 8,270,781, the contents of which are herein incorporated by reference in their entirety. Such devices can include a photonic circuit integrated monolithically with microfluidic channels, such that the optical interrogation zones are in the proximity of and well aligned to the optical waveguides that collect fluorescence and/or scattering light signals. In some embodiments, multiple waveguides are employed to form an array waveguide structure so that, along the direction of flow, a particle (e.g., a cell) will pass a series of waveguide-defined optical interrogation zones, each producing a signal that is correlated in time and space to the others.

Cell Purification Module

Another component of the modular bedside systems described herein, and depicted in FIG. 3, is a "cell purification module" (460). During use of the systems described herein, a cell purification module (460) can receive the "customized" or "modified" (e.g., CAR T) cells from any of the embodiments of the cell customization modules described herein. The cell purification module is designed and configured to receive the customized or modified (e.g., CAR T) cells, and further purify such cells or cell populations prior to their reentering the patient via the outlet conduit.

Many of the techniques and devices described herein for use with the cell separation module (200), including those used in the enrichment unit (1100), are also applicable for use with the cell purification module (460). Accordingly, purification techniques that can be used in the cell purification module include, but are not limited to magnetic separation, centrifugation, filtration, immunoaffinity separation, gravitation separation, density gradient separation, elutriation, and combinations thereof.

In some embodiments, the cell purification module (460) can comprise a centrifuge for processing the customized and/or modified (e.g., CAR T) cells from the cell customization module and/or the sampling or holding unit.

The cell purification module (460) can comprise, in some embodiments, an enrichment unit (1100), that enriches for the customized and/or modified (e.g., CAR T) cells from the cell customization module and/or the sampling unit. The enrichment of the customized and/or modified (e.g., CAR T) cells can be to enrich to a percentage purity of (e.g., CAR T) cells and/or eliminate a particular cell type, e.g., non-modified cells, from the population prior to being reintroduced into the patient via the outlet conduit.

Filters, filtering systems, methods, and devices can also be components of the cell purification module (460) described herein, in some embodiments. In some embodiments, a filtration chamber used in the cell purification module is a chamber that comprises or engages at least one microfabricated filter enclosed in a housing. The surface of the filter and/or the inner surface of the housing can be modified by vapor deposition, sublimation, vapor-phase surface reaction, or particle sputtering to produce a uniform coating, in some embodiments. A filtration chamber can comprise one or more fluid-impermeable materials, such as but not limited to, metals, polymers, plastics, ceramics, glass, silicon, or silicon dioxide. Preferably, a filtration chamber has a volumetric capacity of from about 0.01 milliliters to about ten liters, more preferably from about 0.2 milliliters to about two liters. In some preferred embodiments, a filtration chamber can have a volume of from about 1 milliliter to about 80 milliliters.

Treatment or modifications can be made to the surface of a microfabricated filter and/or the inner surface of a housing that encloses the microfabricated filter to improve its filtering efficiency.

A filter and/or filter chamber used in a cell purification module (460) can be physically or chemically treated, for example, to alter surface properties (e.g., hydrophobic, hydrophilic), and thereby reduce the interaction of sample components with the filter and/or housing surface, in some embodiments. As described elsewhere herein, vapor deposition, sublimation, vapor-phase surface reaction, or particle sputtering are some of the methods that can be used to treat or modify the surface of a filter and/or filter chamber.

A filtration chamber can also comprise a component that comprises electromagnetic elements. Such electromagnetic elements can be used for the capture of sample components before or, preferably, after, filtering of the sample. Sample components can be captured after being bound to magnetic beads. The captured sample components can be either undesirable components to be retained in the chamber after the sample containing desirable components has already been removed from the chamber, or the captured sample components can be desirable components captured in the chamber after filtration.

In some embodiments of the systems and methods described herein, purification of (e.g., CAR T) cells from the cell customization module and/or sampling and/or holding unit can be by chemical or physical means. Such purification procedures can employ one or more methods known in the art including, without limitation, antigen capture, beads, magnetics, fluorescent-activated cell sorting, microfluidics, solid support, acoustics, bioluminescence, antibody tagging, or enzyme substrates. For example, markers or determinants specific for the customized and/or modified (e.g., CAR T) cell populations can be used to isolate or enrich for these cells. Where magnetic beads are used, in some embodiments, the customized and/or modified (e.g., CAR T) cell populations are still coupled with the microbead-bound antibodies when they reenter the patient through the outlet conduit.

The cell purification module (460) can also use acoustophoretic filtering device, as described in US Patent Publication 20170204360, the contents of which are herein incorporated by reference in their entirety. Standing waves can be used to trap the modified (e.g., CAR T) cells present in fluid moving from the cell customization module. The modified (e.g., CAR T) cells, having a positive contrast factor, move to the nodes (as opposed to the anti-nodes) of the standing wave. As the cells and cell debris agglomerate at the nodes of the standing wave, there is also a physical scrubbing of the fluid that occurs, whereby more cells are trapped as they come in contact with the cells that are already held within the standing wave. This generally separates the modified cells from the fluid. When the cells in the standing wave agglomerate to the extent where the mass is no longer able to be held by the acoustic wave, the aggregated cells that have been trapped can fall out of the fluid stream through gravity, and can be collected separately. Desirably, the ultrasonic transducer(s) generate a multi-dimensional (e.g., three-dimensional) standing wave in the fluid that exerts a lateral force on the suspended particles to accompany the axial force so as to increase the particle trapping capabilities of the acoustophoretic filtering device.

Such acoustic filtering devices used with the systems and methods described herein are designed to maintain a high intensity three-dimensional acoustic standing wave. Such devices are driven by a function generator and amplifier. It can be desirable, in some embodiments, due to acoustic streaming, to modulate the frequency or voltage amplitude of the standing wave. This modulation can be done by amplitude modulation and/or by frequency modulation. The duty cycle of the propagation of the standing wave can also be utilized to achieve certain results for trapping of specific cells or cell populations.

Kits and Consumables

According to the presently contemplated bedside systems, a variety of kits are contemplated. According to the most frequently contemplated embodiments, each kit is fully integrated to provide the reagents to provide customized cell-based therapies and treatments in a patient-connected, closed-loop continuous-flow manner, including cellular modifications and treatments. The presently contemplated kits are provided in a manner that permits the use of a single system for multiple different cell customization treatments (including in certain embodiments—different types of cell customizations) for one or more different patients without the risk of cross-contamination. For example, no blood or blood component touching parts are reused between treatments or patients. In often included embodiments, the system is set up for use by attaching a kit to the cell separation module (200) and/or cell customization module (400). In certain embodiments, separate kits are utilized for the cell separation module (200) and/or cell customization module (400). In certain other embodiments, a single kit is used for the cell separation module (200) and the cell customization module (400). The processor (600) and/or user of the system often verifies proper attachment and, if necessary, conducting of a priming or initialization sequence prior to use.

The presently contemplated kits include conduits for fluid flow between devices and/or modules of the system. Such kits also often include one or more fluid sampling port and/or one or more drug/genetic material administration port in the location(s) relative to the system noted elsewhere herein. The kits also often include reagents necessary for the cell separation and/or cell customization resident in the kit such that drug/genetic material is not required to be added after connecting the kit with the system. The kits also include connectors to connect the kits in operable connection with the system to permit blood flow from the patient to the system, cell separations in the cell separation module (200), cell customizations in the cell customization module (400), and passage of the blood, cells and/or blood components back to the patent in a patient-connected, closed-loop continuous-flow manner. Such kits also often include one or more areas for detector access to the kit or system while in use such that the cells or fluid flowing or resident in the system can be examined by the detector. The locations for such detector access and adaptations necessary to permit the desired type of detection (e.g., luminescence, fluorescence, light scatter, etc.) are in accordance with the locations described elsewhere herein.

Processor Module and Related Systems and Methods

It is understood that the systems described herein include circuitry and elements necessary to regulate and control the activities carried out in the various modules, the totality of which is termed herein the "processor module" (600). The circuitry can include one or more of a microprocessor, or any other such component capable of controlling the activities carried out in the various modules, and a storage device or device capable of storing the data and/or transmitting data to a remote storage location. The remote location can be a local or remote server or databank, or a cloud-based storage system. In some embodiments, the circuitry can be operatively coupled to one or more input and output devices, for example an actuator, a motor-controlled valve, a motor, an accelerometer, a load sensor, a light source, or a light detector. In frequently contemplated embodiments, the systems contemplated herein include a graphical user interface (GUI) as one of a plurality of user-based input devices. The GUI may be imparted with a variety of functionalities, including actuation/control of the system, a module within the system, or a device within the system. As such, the GUI is placed in operable and/or data accessibility connection with the processor module (600). The systems also may be employed with accessibility from a remote location to control, monitor, and/or troubleshoot one or more components, modules, or devices in the system. The circuitry can comprise one or more microcontrollers. In some embodiments, the circuitry is configured to receive input from at least one module. Circuitry can be configured, for example, to cause a motor to adjust one or more valves controlling flow-through between the various modules, such that a fluid path is opened between the modules. In some embodiments, the circuitry causes the flow-through between two different modules to open and close after a pre-determined interval. In some embodiments, the total amount of time where flow-through is permitted between two given modules is tracked and/or stored by the circuitry. The processor module (600) enables monitoring and process control of key activities including but not limited to in-line testing for quality, safety and other clinical purposes conducted, product dosing and cellular product quality conducted while patient-connected to cell separator (1200) (e.g. apheresis device) throughout process.

Some embodiments of the processor module (600) include monitoring and/or recording and/or analyzing electronic signals. It is to be understood that such devices can include analog and/or digital signals. Thus, while a given module or component thereof sensor may be monitored and/or connected to circuitry, the circuitry can, in some embodiments, only intermittently sample, record, and or process such data. In some embodiments, continuous monitoring can include intermittent monitoring at set intervals.

In frequent embodiments the processor module (600) is placed in operable connection with the detectors (500) to control and/or monitor the status, operation and/or function of one or more detector. Although FIG. 1 depicts detectors (500) as a separate module, it is understood that this is for simplicity of demonstration only. In practice, one or more detector contemplated here will be placed in operable communication with the cell separation module (200) or cell customization module (400), the cell washing unit (310), a conduit between the modules, or an aspect thereof, such that it can perform a detection operation. In this regard, such a detector is often closely associated with, or part of, the specific module (e.g., the cell separation module (200) or cell customization module (400), or conduit before or after cell entry to or exit from a module, where the detection is occurring rather than as a stand-alone detector module. In basically all such embodiments, the detector or plurality of detectors associated with one or more different modules or devices of the system is/are in operable connection with the processor to control and/or monitor the status, operation and/or function of the detector(s). Data obtained from the detector may be stored on the processor or an associated data storage system in data communication connection with the detector or processor. In certain embodiments, data collected by the detector is transmitted to a data storage location without passing through a processor resident on the system.

In frequent embodiments the processor module (600) is placed in operable connection with the cell separation module (200) to control and/or monitor the status, operation and/or function of cell separation, cell washing, and/or cell enrichment. Information obtained from the sampling unit (450A) may also be input to the processor module (600) to record or adjust an aspect or function of device within the cell separation module (200). For example, the cell separator (1200) (e.g., apheresis device) completes one or more mononuclear separation cycles then sends signal to the processor (600) that it is complete; then the processor (600) signals to a pump to move cellular materials to a cell washing unit (210). Often this is performed prior to a cell exiting the cell separation module (200).

In frequent embodiments the processor module (600) is placed in operable connection with the cell washing unit (310) or a conduit or flow path within the system to control and/or monitor the status, operation and/or function of cell washing, and/or cell/fluid flow rate or direction.

In frequent embodiments the processor module (600) is placed in operable connection with the cell customization module (400) to control and/or monitor the status, operation and/or function of purification, drug/genetic material administration, electroporation, microfluidic transfection, lipofection, cell washing, and/or incubation. Information obtained from the sampling unit (450B) may also be input to the processor module (600) to record or adjust an aspect or function of device within the cell customization module (400). For example, once an electroporation step is complete, the electroporation module (420) sends signal to the processer (600) that it is complete; then the processor (600) signals to a pump to move transfected cellular material to the cell washing unit (410). Also, for example, once a microfluidic module step is complete, the microfluidic module (421) sends signal to the processer (600) that it is complete; then the processor 600 signals to a pump to move transfected cellular material to the cell washing unit (410). Also, for example, once a lipofection module step is complete, the lipofection module (422) sends signal to the processer (600) that it is complete; then the processor (600) signals to a pump to move transfected cellular material to the cell washing unit (410). Often this is performed prior to a cell exiting the cell customization module (400).

Remote operation and/or monitoring of the system or a module or device located on the system is included in the presently contemplated embodiments. In this regard, aspects of the device including fluid flow positions, directions and rates, valve actuation, pump operation, conduit connectivity, consumable or kit connectivity or status, detector operation, cell resident times, incubation operation, time and status, purification operation, time and status, electroporation module operation, time and status, microfluidic module operation, time and status, lipofection module operation, time and status, drug/genetic material administration, cell washing operation, time and status, incubator or temperature control mechanism operation, time and status, cell separation operation, time and status, cell enriching operation, time and status, processor and storage operation, time and status may be remotely operated or monitored. Technicians, physicians, regulatory personnel, patients, and other medical care personnel may conduct such remote operation. While the system is bedside with the patient, one or more systems may be operated and/or monitored from a location remote from the patient, for example, at a health care staff monitoring/services station or within the local health care facility or remotely from a different location. In another example, a system technician or database accessible to such a technician, is provided with diagnostic or operation information from the system for maintenance or repair of the herein described systems through the processor (600).

Methods of Treatment Using Bedside Systems

The systems described herein are useful for treatment of a variety of diseases and conditions, particularly for those diseases and conditions involving blood cells, needing immunomodulation, and/or having systemic involvement. Immunomodulatory conditions include, e.g., enhancing an immune response patient in need of enhanced immune responses, such as enhancing an immune response in a subject who is immunocompromised or enhancing an antitumor response by activating one or more immune cell populations; reducing an inflammatory response, e.g., to treat an autoimmune disease or reduce organ or tissue rejection, by reducing activation in one or more immune cell populations. For example, activated and loaded dendritic cells and other antigen-presenting cells can be used in treating cancer, infectious diseases, and immunodeficiency diseases. Activated NK cells can be used to treat cancer Enhancement of T-regulatory cell numbers and/or regulatory functions can be used for treating graft versus host disease (GvHD), immunodeficiency diseases, atopic dermatitis and asthma. Activated, antigen-specific, and/or chimeric antigen receptor (CAR) T cells, including cytotoxic T lymphocytes (CTLs), helper T cells, and regulatory T cells, can be used in treating cancer, infectious diseases and allergies.

The systems described herein are also useful for treatment of a variety of diseases and conditions, particularly for those diseases and conditions having specific antigens that can be targeted using chimeric antigen receptors. Thus, activated, antigen-specific, chimeric antigen receptor (CAR) T cells, including cytotoxic T lymphocytes (CTLs), helper T cells, and regulatory T cells, can be used in treating cancer, infectious diseases and allergies using the systems and methods described herein. Accordingly, in some embodiments, the systems and methods described herein are used for treating a patient having a cancer or tumor. The enrichment and expansion of antigen-specific CTLs ex vivo for adoptive transfer to the patient provides for a robust anti-tumor immune response. Cancers that can be treated or evaluated according to the methods include cancers that historically illicit poor immune responses or have a high rate of recurrence. Exemplary cancers include various types of solid tumors, including carcinomas, sarcomas, and lymphomas. In various embodiments the cancer is melanoma (including metastatic melanoma), colon cancer, duodenal cancer, prostate cancer, breast cancer, ovarian cancer, ductal cancer, hepatic cancer, pancreatic cancer, renal cancer, endometrial cancer, testicular cancer, stomach cancer, dysplastic oral mucosa, polyposis, head and neck cancer, invasive oral cancer, non-small cell lung carcinoma, small-cell lung cancer, mesothelioma, transitional and squamous cell urinary carcinoma, brain cancer, neuroblastoma, and glioma. In some embodiments, the cancer is a hematological malignancy, such as chronic myelogenous leukemia, childhood acute leukemia, non-Hodgkin's lymphomas, chronic lymphocytic leukemia, malignant cutaneous T-cells, mycosis fungoids, non-MF cutaneous T-cell lymphoma, lymphomatoid papulosis, T-cell rich cutaneous lymphoid hyperplasia, and discoid lupus erythematosus.

In some embodiments the systems and methods described herein are used for treating a patient having sickle cell anemia, hemophilia, or beta-thalassemia.

In some embodiments, the systems and methods described herein are used for treating a patient having an infectious disease. The infectious disease can be one in which enrichment and expansion of antigen-specific immune cells (such as CD8+ or CD4+ T cells) or other cell populations can enhance or provide for a productive immune response. Infectious diseases that can be treated include those caused by bacteria, viruses, prions, fungi, parasites, helminths, etc. Such diseases include AIDS, hepatitis, CMV infection, and post-transplant lymphoproliferative disorder (PTLD). CMV, for example, is the most common viral pathogen found in organ transplant patients and is a major cause of morbidity and mortality in patients undergoing bone marrow or peripheral blood stem cell transplants. This is due to the immunocompromised status of these patients, which permits reactivation of latent virus in seropositive patients or opportunistic infection in seronegative individuals. A useful alternative to these treatments is a prophylactic immunotherapeutic regimen involving the generation of virus-specific CTL derived from the patient or from an appropriate donor before initiation of the transplant procedure. PTLD occurs in a significant fraction of transplant patients and results from Epstein-Barr virus (EBV) infection. EBV infection is believed to be present in approximately 90% of the adult population in the United States. Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers.

In some embodiments, the systems and methods described herein are used for treating a patient having an autoimmune disease, in which enrichment and expansion of regulatory T cells (e.g., CD4+, CD25+, Foxp3+) could dampen the deleterious immune response. Autoimmune diseases that can be treated include systemic lupus erythematosus, rheumatoid arthritis, type I diabetes, multiple sclerosis, Crohn's disease, ulcerative colitis, psoriasis, myasthenia gravis, Goodpasture's syndrome, Graves' disease, pemphigus vulgaris, Addison's disease, dermatitis herpetiformis, celiac disease, and Hashimoto's thyroiditis.

Cell Customization Via Electroporation

In this example, nucleated blood cells are pumped from the cell separation module (200) to a cell washing module that washes and suspends the cells in electroporation buffer (8 mM $Na_2HPO_4$, 2 mM $KH_2PO_4$, 1 mM $MgSO_4 \cdot 7H_2O$ and 250 mM sucrose, pH 7.4) at a concentration of about $2 \times 10^6$ cells/ml. The washed cells suspended in electroporation buffer are pumped into a flow-through electroporation cassette formed of PDMS adhered to a glass substrate essentially as described in Gung et al., J. Controlled Release 144: 91-100 (2010). The tubing immediately upstream of the electroporation cassette includes a Venturi port connected to a reservoir of supercoiled plasmid DNA encoding GFP as a transfection marker, at 50 µg/ml.

The flow-through electroporation cassette includes five narrow sections of 500 µm wide in the flow channel, alternating with wider sections of 7,500 µm. The cassette is pre-loaded with electroporation buffer.

Constant DC voltage is applied to the flow-through electroporation cassette, and cell suspension, admixed via the Venturi port with plasmid DNA is pumped into the flow-through cassette. Cells emerging from the cassette enter a conduit or tubing that leads the cells either to the patient, or to a holding, collection, incubating or sampling unit where they are held or incubated to permit recovery from the electroporation process and/or analysis, sampling or detection, e.g., fluorescence detection for GFP, to detect or monitor transfection before being reintroduced to the patient. The cells can be admixed with saline or plasma, with or without additional factors or nutrients in the holding, collecting, incubating or sampling unit.

Cell Customization by Squeeze Transfection

A system in which squeeze microfluidic transfection can be used to customize cells as follows.

In this example, a nucleated blood cell fraction enriched for dendritic cells is pumped from the enrichment unit (1100) in the cell separation module (200) to a microfluidic module (421) of the cell customization module (400), where the cells are mixed with plasmid DNA nanoparticles encoding GFP in a manner similar to that employed in an electroporation module (420). Plasmid DNA nanoparticles are prepared as described in US2014287509, incorporated herein by reference in its entirety. Cells are optionally mixed with a surrogate marker for customization, e.g., nanoparticles that fluoresce at an excitation and/or emission wavelength distinguishable from the GFP.

The dendritic cell/nanoparticle DNA suspension is pumped under conditions described in the '509 publication through an array of 50 microfluidic squeeze channels as described in the '509 publication, arranged in parallel and including constrictions to about 60% of dendritic cell diameter.

Cells exiting the array of microfluidic squeeze channels are passed to a cell purification unit (460), that removes unincorporated nanoparticles, then collected in a holding unit (900) interfaced with a fluorescence detector, where they are held until GFP fluorescence and/or surrogate marker fluorescence is detected at 20× background. Once this fluorescence threshold is reached, customized cells can be admixed with saline or plasma, with or without additional factors or nutrients, and returned to the patient via outlet conduit 700.

The above examples and embodiments are included for illustrative purposes only and are not intended to limit the scope of the disclosure. Many variations to those methods, systems, kits, and devices described above are possible. Since modifications and variations to the examples described above will be apparent to those of skill in this art, it is intended that this invention be limited only by the scope of the appended claims. All publications and references cited herein are expressly incorporated herein by reference in their entirety and/or for the specific reason for which they are cited herein.

The invention claimed is:

1. A subject-connected, closed-loop system for the modification of a cell, the system comprising:
   a) an inlet conduit adapted for parenteral communication with the subject and adapted for receiving blood from the subject;
   b) a cell separation module in fluid communication with the inlet conduit, the cell separation module comprising a cell separator configured to produce a fraction enriched in a target nucleated blood cell type using the blood from the subject, and the cell separation module further comprising a first sampling unit for obtaining a sample of the fraction;
   c) a cell customization module in fluid communication with the cell separation module so as to receive the nucleated blood cell fraction enriched in the target cell type from the cell separation module, the cell customization module configured to present one or more modifying agents to the target nucleated blood cells, thereby generating modified cells, and the cell customization module further comprising a second sampling unit for obtaining a sample of the modified cells, wherein the cell customization module comprises a conduit that permits a first batch of target cells treated with a modifying agent to pass into a temperature-controlled holding unit while a second batch is treated with modifying agent;
   d) a detector configured to conduct a detection operation and operably interfaced with the cell separation module, the cell customization module, operably interfaced between the cell separation module and the cell customization module, and/or operably interfaced between the cell customization module or the cell separation module and the subject;
   e) an outlet conduit adapted for parenteral communication with the subject and for conducting modified target cells parenterally to the subject; and f) a processor configured to control an operation of the inlet conduit, the cell separation module, the cell customization module, the detector, or the outlet conduit of the system;

wherein the inlet conduit, the cell separation module, the cell customization module, the detector, and the outlet conduit of the system are connected in a fluid-sealed closed-loop adapted for parenteral connection with a patient at both ends of the fluid sealed closed-loop, and the system is configured to permit cell separation, delivery of a modifying agent to the target nucleated blood cell type and delivery of the modified cells to the subject in real time within the fluid sealed closed-loop.

2. The system of claim 1, wherein the cell customization module comprises:

(a) a temperature control unit capable of reaching and maintaining temperatures within the unit of between 0° C. and 37° C., inclusive; a cell washing unit comprising a chamber that mixes target nucleated blood cells with at least one wash solution that dilutes or removes a plasma component from the target nucleated blood cells and places washed cells into suspension prior to their modification; an inlet for introducing a nucleic acid preparation to the suspension of washed cells, or a chamber comprising a nucleic acid preparation into which a washed cell suspension is introduced; and an electroporation chamber, connected to a power source effective to electroporate the nucleic acid into a target nucleated blood cell, wherein temperature control unit, the cell washing unit, and the electroporation chamber are positioned in the temperature control unit;

(b) a temperature control unit capable of reaching and maintaining temperatures between 4° C. and 37° C., inclusive; a cell-washing unit comprising a chamber that mixes target nucleated blood cells with at least one wash solution that dilutes or removes a plasma component from the target nucleated blood cells and places washed cells into suspension prior to their modification; and an inlet for introducing a nucleic acid preparation to the suspension of washed cells, or a chamber comprising a nucleic acid preparation into which a washed cell suspension is introduced, the nucleic acid preparation comprising a lipid transfection reagent;

(c) a chamber in fluid communication with and configured to receive a suspension of enriched target nucleated blood cells from the cell separation module, the chamber comprising an inlet for the introduction of a modifying agent or comprising a preparation of modifying agent, and a plurality of microfluidic channels that narrow over their length to at least 20-99% of the diameter of the enriched target nucleated blood cells; and a source of pressure sufficient to squeeze suspended cells through the plurality of microfluidic channels in the presence of the modifying agent;

(d) a temperature control unit capable of reaching and maintaining temperatures between 4° C. and 37° C., inclusive; a cell-washing unit comprising a chamber that mixes target nucleated blood cells with at least one wash solution that dilutes or removes a plasma component from the target nucleated blood cells and places washed cells into suspension prior to their modification; and an inlet for introducing one or more modifying agents to the suspension of washed cells, or a chamber comprising one or more modifying agents into which a washed cell suspension is introduced, thereby allowing contacting of the washed cells with the one or more modifying agents; or (e) a temperature control unit capable of reaching and maintaining temperatures between 4° C. and 37° C., inclusive; a cell-washing unit comprising a chamber that mixes target nucleated blood cells with at least one wash solution that dilutes or removes a plasma component from the target nucleated blood cells and places washed cells into suspension prior to their modification; and an inlet for introducing one or more modifying agents in a membrane disruptive delivery solution to the suspension of washed cells, or a chamber comprising one or more modifying agents in a membrane disruptive delivery solution into which a washed cell suspension is introduced thereby allowing contacting of the washed cells with the one or more modifying agents in the membrane disruptive solution.

3. The system of claim 2, wherein the cell customization module interfaces with a detector module.

4. The system of claim 3, further comprising a sampling unit configured to obtain or receive an aliquot of the fraction or the modified cells from the cell separation module or the cell customization module.

5. The system of claim 4, wherein the sampling unit interfaces with the detector and the detector is configured to detect and count modified cells and send a signal to the processor when the aliquot comprises a predetermined threshold of modified cells.

6. The system of claim 4, wherein the cell customization module is configured to allow for batch-flow operation.

7. The system of claim 1, wherein the cell separation module comprises a leukapheresis module that separates nucleated blood cells from a nuclear red blood cells, and a selection unit for further selecting a subset of target nucleated blood cells to enter the cell customization module.

8. The system of claim 7, wherein the selection unit comprises a reagent that specifically binds a cell-surface determinant on nucleated blood cells other than the subset of target nucleated blood cells or a reagent that specifically binds a cell-surface determinant present on the subset of target nucleated blood cells, thereby selectively enriching for the subset of target nucleated blood cells.

9. The system of claim 7, wherein the selection unit selects the subset of target nucleated blood cells using one or more parameters selected from cell size, cell shape, cell granularity, cell buoyancy, cell acoustics, and cell density.

10. The system of claim 1, further comprising a cell purification module for selecting the modified cells.

11. The system of claim 7, wherein the modifying agent is selected from a small molecule agent, a biologic agent, a protein or peptide, a nucleic acid, a chimeric T cell receptor, and a Clustered Regularly Interspaced Short Palindromic Repeats (CRISPR) enzyme comprising one or more nuclear localization sequences.

12. The system of claim 1, wherein the system comprises a bedside system adapted for treatment of a disease or condition involving blood cells, needing immunomodulation, and/or having systemic involvement.

13. The system of claim 1, wherein the processor module is placed in operable connection with:

the detector to control and/or monitor the status, operation and/or function of one or more detector;

the cell separation module to control and/or monitor the status, operation and/or function of cell separation, cell washing, and/or cell enrichment;

the cell washing unit or a conduit or flow path within the system to control and/or monitor the status, operation and/or function of cell washing, and/or cell/fluid flow rate or direction; and/or the cell customization module to control and/or monitor the status, operation and/or function of purification, drug/genetic material administration, electroporation, microfluidic transfection, lipofection, cell washing, and/or incubation.

14. A subject-connected, closed-loop system for the modification of a cell, the system comprising:
a) an inlet conduit adapted for parenteral communication with the subject and adapted for receiving blood from the subject;
b) a cell separation module in fluid communication with the inlet conduit, the cell separation module comprising a cell separator configured to produce a fraction enriched in a target nucleated blood cell type using the blood from the subject, and the cell separation module further comprising a first sampling unit for obtaining a sample of the fraction;
c) a cell customization module in fluid communication with the cell separation module so as to receive the nucleated blood cell fraction enriched in the target cell type from the cell separation module, the cell customization module configured to present one or more modifying agents to the target nucleated blood cells, thereby generating modified cells, and the cell customization module further comprising a second sampling unit for obtaining a sample of the modified cells, wherein the cell customization module is configured to deliver one or more nucleic acids encoding a chimeric antigen receptor (CAR) to the target nucleated blood cells, thereby generating CAR T cells; and wherein the system is further configured to permit cell separation, delivery of a nucleic acid encoding a CAR to a target cell type to generate CAR T cells, and return of CAR T cells to the subject in real time in a closed loop;
d) a detector configured to conduct a detection operation and operably interfaced with the cell separation module, the cell customization module, operably interfaced between the cell separation module and the cell customization module, and/or operably Interfaced between the cell customization module or the cell separation module and the subject;
e) an outlet conduit adapted for parenteral communication with the subject and for conducting modified target cells parenterally to the subject; and
f) a processor configured to control an operation of the inlet conduit, the cell separation module, the cell customization module, the detector, or the outlet conduit or the system;

wherein the inlet conduit, the cell separation module, the cell customization module, the detector, and the outlet conduit of the system are connected in a fluid-sealed closed-loop adapted for parenteral connection with a patient at both ends of the fluid sealed closed-loop, and the system is configured to permit cell separation, delivery of a modifying anent to the target nucleated blood cell type and delivery of the modified cells to the subject in real time within the fluid sealed closed-loop.

15. A method of introducing a modification to a target nucleated blood cell, the method comprising:
parenterally connecting a subject in need of such modification to the system of claim 1, via the inlet and outlet conduits;
permitting the blood of the subject to flow into the cell separation module and producing a fraction enriched in a target nucleated blood cell type;
permitting a blood cell fraction enriched in the target cell type to flow from the cell separation module to the cell customization module and contacting the blood cell fraction enriched in the target cell type with one or more modifying agents, thereby generating modified cells; and
permitting the modified cells to parenterally flow to the subject via the outlet conduit.

16. The method of claim 15, further comprising a step of operably connecting a single use cassette or system kit adapted to introduce the modification to the target nucleated blood cell with the system.

17. The method of claim 15, wherein an operation of the system or a module thereof is controlled or monitored using a processor module, wherein the processor is remotely controlled or monitored.

18. The method of claim 15, wherein the one or more modifying agents comprises:
(a) a small molecule agent, a biologic agent, a protein or peptide, a nucleic acid, or a CRISPER enzyme comprising one or more nuclear localization sequences; or
(b) one or more nucleic acids encoding a chimeric antigen receptor (CAR), thereby generating CAR T cells.

19. The method of claim 15, wherein the subject in need of such modification comprises a subject afflicted with cancer, sickle cell anemia, hemophilia and/or beta-thalassemia, and the method is adapted to treat the cancer, sickle cell anemia, hemophilia and/or beta-thalassemia.

\* \* \* \* \*